United States Patent
Koh et al.

(10) Patent No.: US 7,371,220 B1
(45) Date of Patent: May 13, 2008

(54) SYSTEM AND METHOD FOR REAL-TIME APNEA/HYPOPNEA DETECTION USING AN IMPLANTABLE MEDICAL SYSTEM

(75) Inventors: Steve Koh, South Pasadena, CA (US); Euljoon Park, Valencia, CA (US); Michael Benser, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 651 days.

(21) Appl. No.: 10/883,857

(22) Filed: Jun. 30, 2004

(51) Int. Cl.
A61B 5/08 (2006.01)

(52) U.S. Cl. ..................................... 600/529

(58) Field of Classification Search ............... 600/529, 600/533
See application file for complete search history.

(56) References Cited

U.S. PATENT DOCUMENTS

| | | | | |
|---|---|---|---|---|
| 4,365,636 A | * | 12/1982 | Barker | 600/529 |
| 4,830,008 A | * | 5/1989 | Meer | 607/42 |
| 5,056,519 A | | 10/1991 | Vince | 128/419 G |
| 5,146,918 A | | 9/1992 | Kallok et al. | 128/419 G |
| 5,275,171 A | | 1/1994 | Barcel | 607/122 |
| 5,483,969 A | * | 1/1996 | Testerman et al. | 600/529 |
| 5,540,732 A | | 7/1996 | Testerman | 607/42 |
| 5,540,733 A | * | 7/1996 | Testerman et al. | 607/42 |
| 5,694,939 A | * | 12/1997 | Cowings | 600/484 |
| 5,817,135 A | | 10/1998 | Cooper et al. | 607/17 |
| 5,824,020 A | * | 10/1998 | Cooper | 607/17 |
| 5,911,218 A | | 6/1999 | DiMarco | 128/200.24 |
| 6,240,316 B1 | | 5/2001 | Richmond et al. | 607/42 |
| 6,331,536 B1 | | 12/2001 | Radulovacki et al. | 514/214.02 |
| 6,345,202 B2 | | 2/2002 | Richmond et al. | 607/42 |
| 6,415,183 B1 | | 7/2002 | Scheiner et al. | 607/42 |
| 6,432,956 B1 | | 8/2002 | Dement et al. | 514/252.1 |
| 6,519,493 B1 | | 2/2003 | Florio et al. | 607/9 |
| 6,525,073 B2 | | 2/2003 | Mendel et al. | 514/337 |
| 6,586,478 B2 | | 7/2003 | Ackman et al. | 514/738 |
| 6,587,725 B1 | | 7/2003 | Durand et al. | 607/42 |
| 6,641,542 B2 | | 11/2003 | Cho et al. | 600/529 |
| 6,881,192 B1 | * | 4/2005 | Park | 600/529 |
| 7,070,568 B1 | * | 7/2006 | Koh | 600/508 |
| 7,082,331 B1 | * | 7/2006 | Park et al. | 607/42 |
| 7,094,207 B1 | * | 8/2006 | Koh | 600/529 |
| 7,155,278 B2 | * | 12/2006 | King et al. | 607/2 |
| 7,179,229 B1 | * | 2/2007 | Koh | 600/485 |
| 2002/0193697 A1 | | 12/2002 | Cho et al. | 600/529 |
| 2002/0193839 A1 | | 12/2002 | Cho et al. | 607/17 |
| 2003/0130703 A1 | | 7/2003 | Florio et al. | 607/11 |
| 2003/0130704 A1 | | 7/2003 | Florio et al. | 607/11 |

(Continued)

*Primary Examiner*—Robert L. Nasser, Jr.
*Assistant Examiner*—Karen E Toth

(57) ABSTRACT

Techniques are provided for detecting the onset of an episode of apnea/hypopnea substantially in real-time. A moving threshold is generated based on recent respiration cycles and differences are accumulated between amplitudes of new respiration cycles and the moving threshold. Apnea/hypopnea is then detected based upon a comparison of the accumulated differences against a fixed threshold. The technique exploits the fact that many episodes of hypopnea begin with a sharp drop in respiration and many episodes of apnea are preceded by a sharp drop in respiration. By accumulating differences between new respiration amplitudes and a short term moving average, any sharp drop in respiration is thereby promptly detected. In many cases, by the time the amplitudes of individual respiration cycles drop to levels directly indicative of apnea/hypopnea, the episode of apnea/hypopnea will have already been detected based upon the sudden sharp drop in respiration amplitude and therapy will have already been initiated.

34 Claims, 13 Drawing Sheets

U.S. PATENT DOCUMENTS

| | | |
|---|---|---|
| 2003/0171781 A1 | 9/2003 | Florio et al. .................. 607/17 |
| 2003/0171782 A1 | 9/2003 | Florio et al. .................. 607/19 |
| 2004/0134496 A1* | 7/2004 | Cho et al. .............. 128/204.23 |
| 2005/0085865 A1* | 4/2005 | Tehrani ....................... 607/42 |
| 2005/0119586 A1* | 6/2005 | Coyle et al. ................ 600/538 |
| 2005/0148897 A1* | 7/2005 | Cho et al. ................... 600/533 |

* cited by examiner

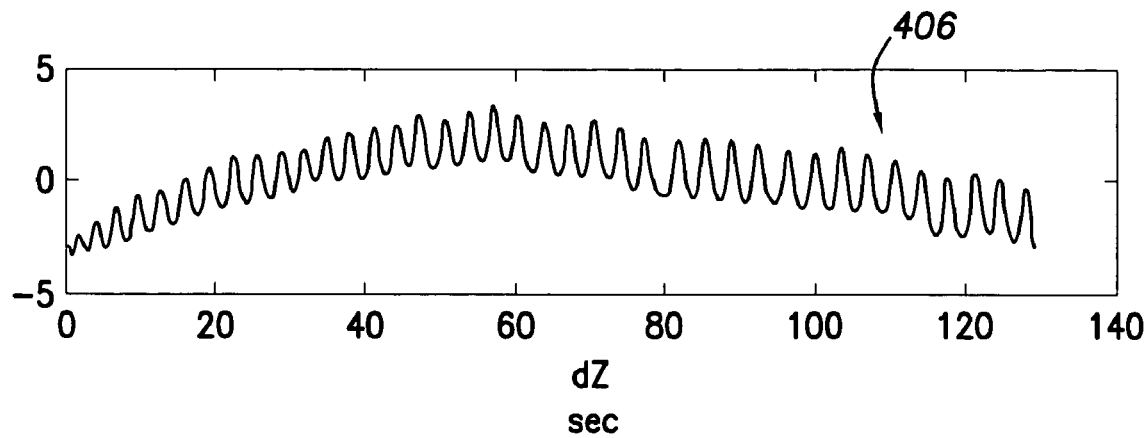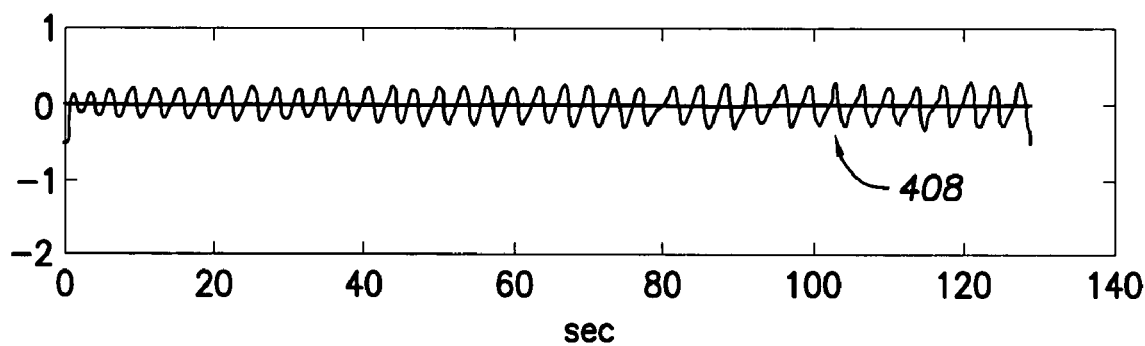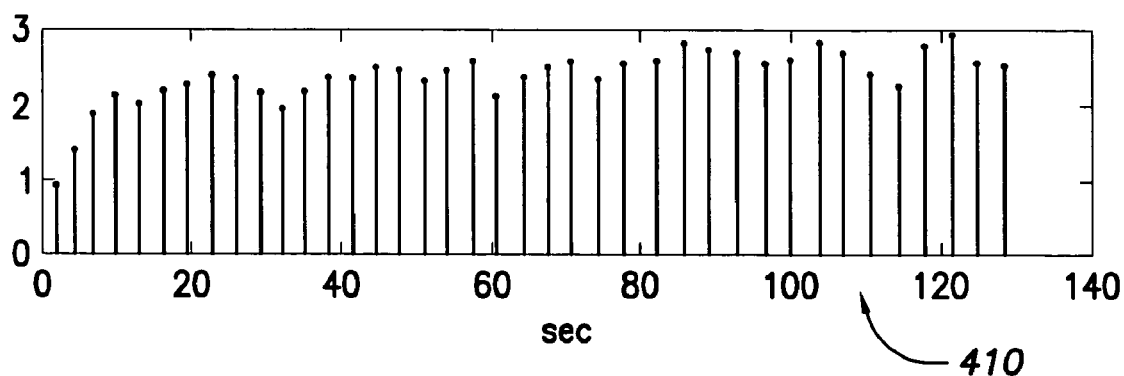
FIG. 8

SYSTEM AND METHOD FOR REAL-TIME APNEA/HYPOPNEA DETECTION USING AN IMPLANTABLE MEDICAL SYSTEM

FIELD OF THE INVENTION

The invention generally relates to implantable medical devices, such as pacemakers or implantable cardioverter/defibrillators (ICDs), and in particular to techniques for detecting apnea or hypopnea in real-time within a patient in which a medical device is implanted and for delivering therapy in response thereto.

BACKGROUND OF THE INVENTION

Apnea and hypopnea are characterized by periods of significantly reduced respiration. With hypopnea, respiration is reduced but is still present. With apnea, however, respiration may cease completely for a minute or longer. One common form of apnea is sleep apnea, in which individual episodes of apnea can occur hundreds of times during a single night. Accordingly, patients with sleep apnea experience periodic wakefulness at night and excessive sleepiness during the day. In addition, apnea can exacerbate various medical conditions, particularly congestive heart failure (CHF) wherein the patient suffers from poor cardiac function. Other medical conditions that can be adversely affected by sleep apnea include: high blood pressure, risk for heart attack and stroke, memory problems, impotency and sexual dysfunction, migraine headaches, depression and anxiety, polycythemia (increase in the number of red blood cells), cor pulmonale (an alteration in the structure and function of the right ventricle caused by a primary disorder of the respiratory system), bradycardia (excessively slow heart rate), tachycardia (excessively fast heart rate), pulmonary hypertension hypoxemia (chronic daytime low blood oxygen) and hypercapnia (increased blood carbon dioxide ($CO_2$)).

One form of sleep apnea is central sleep apnea (CSA), which is believed to be the result of a neurological condition. Briefly, respiration is regulated by groups of nerve cells in the brain in response to changing blood chemistry levels, particularly blood $CO_2$ levels. When blood $CO_2$ levels exceed a certain threshold, the groups of nerve cells generate a burst of nerve signals for triggering inspiration. The inspiration nerve signals are relayed via phrenic nerves to the diaphragm and via other nerves to chest wall muscles, which collectively contract to expand the lungs. With CSA, the nerve signals are not properly generated during extended periods of time while the patient is asleep or are of insufficient magnitude to trigger sufficient muscle contraction to achieve inhalation. In either case, the patient thereby fails to inhale until appropriate inspiration nerve signals are eventually generated—often not until after the patient awakes in response to significantly high blood $CO_2$ levels. Arousal from sleep due to CSA usually lasts only a few seconds, but such brief arousals nevertheless disrupt continuous sleep and can prevent the patient from achieving rapid eye movement (REM) sleep, which is needed. In addition, as already noted, frequent periods of apnea can exacerbate other medical conditions. In particular, aberrant blood chemistry levels occurring by sleep apnea are a significant problem for patients with CHF. Due to poor cardiac function caused by CHF, patients already suffer from generally low blood oxygen levels. Frequent periods of sleep apnea result in even lower blood oxygen levels.

Another form of sleep apnea, which is more common, is obstructive sleep apnea (OSA) wherein the respiration airway is temporarily blocked. With OSA, proper inspiration nerve signals are generated by the brain and so the diaphragm and chest muscles contract in an attempt to cause the lungs to inhale. However, an obstruction of the respiration airway blocks delivery of air to the lungs and so blood $CO_2$ levels continue to increase, usually until the patient awakens and readjusts his or her position so as to reopen the obstructed respiration pathway so that normal breathing can resume. The site of obstruction is usually the soft palate, near the base of the tongue, which lacks rigid structures such as bone or cartilage for keeping the airway open. While the patient is awake, muscles near the soft palate keep the passage open. However, while asleep, the muscles can relax to a point where the airway collapses and hence becomes obstructed. As with CSA, arousal from sleep usually lasts only a few seconds but is sufficient to disrupt continuous sleep and prevent proper REM sleep. It is estimated that OSA occurs in approximately two percent of women and four percent of men over the age of thirty-five. Obesity is a significant contributing factor. In addition, patients are at greater risk of OSA with increasing age, due to loss of muscle mass, particularly within the muscles that would otherwise hold the respiration airway open. Some patients suffer from mixed apnea, wherein episodes of CSA and OSA can occur the same night.

Apnea can also occur during Cheyne-Stokes Respiration (CSR), which is an abnormal respiratory pattern often occurring in patients with CHF. CSR is characterized by alternating periods of hypopnea and hyperpnea (i.e. fast, deep breathing.) Briefly, CSR arises principally due to a time lag between blood $CO_2$ levels sensed by the respiratory control nerve centers of the brain and the blood $CO_2$ levels. With CHF, poor cardiac function results in poor blood flow to the brain such that respiratory control nerve centers respond to blood $CO_2$ levels that are no longer properly representative of the overall blood $CO_2$ levels in the body. Hence, the respiratory control nerve centers trigger an increase in the depth and frequency of breathing in an attempt to compensate for perceived high blood $CO_2$ levels—although the blood $CO_2$ levels have already dropped. By the time the respiratory control nerve centers detect the drop in blood $CO_2$ levels and act to slow respiration, the blood $CO_2$ levels have already increased. This cycle becomes increasingly unbalanced until respiration alternates between hypopnea and hyperpnea. The periods of hypopnea often become sufficiently severe that no breathing occurs between the periods of hyperpnea, i.e. periods of frank apnea occur between the periods of hyperpnea. The wildly fluctuating blood chemistry levels caused by alternating between hyperpnea and apnea/hypopnea can significantly exacerbate CHF and other medical conditions. When CHF is still mild, CSR usually occurs, if at all, only while the patient is sleeping. When it becomes more severe, CSR can occur while the patient is awake. Accordingly, CSR is one mechanism by which apnea can occur within patients who are awake. Apnea can also occur while awake due to neurological disorders or other factors. Hence, apnea is not limited to occurring only within sleeping patients.

In view of the significant adverse consequences of apnea/hypopnea, particularly insofar as patients with CHF are concerned, it is highly desirable to provide techniques for detecting and treating the condition. Apnea/hypopnea arising due to CSR is usually treated by addressing the source of the CSR, such as an underlying CHF. By reducing CHF so as to improve stroke volume, CSR is less likely to occur and so any periods of apnea arising during CSR may be avoided. OSA is usually treated by having the patient wear a breathing apparatus at night, such as a device providing continuous positive airway pressure (CPAP) therapy or bi-level positive pressure therapy (Bi-level-PAP). Surgery, however, is sometimes necessary. Although the source of CSA appears to be neurological, breathing devices employing CPAP or B-PAP techniques have been found to be effective for treating CSA as well. Although such breathing devices are effective when properly employed, they are often uncomfortable and inconvenient for the patient and, as a result, many patients fail to wear the device each night and hence forfeit the benefits thereof. In addition, when properly worn, the devices apply therapy continuously—even on nights when the patient might not have any actual episodes of sleep apnea.

Thus, many of these forms of therapy are delivered more or less continuously, at least while the patient is asleep, even when no episodes of apnea/hypopnea are occurring. In many cases, it would instead be desirable to automatically detect individual episodes of apnea/hypopnea and deliver therapy only as needed. In particular, it would desirable to provide such capability within an implantable medical system. Properly equipped, an implantable medical system could detect the onset of individual episodes of apnea/hypopnea and deliver appropriate therapy. For example, if an episode of OSA is detected, stimulation signals could be delivered to muscles near the soft palate to increase of muscle tone sufficient to reopen the blocked respiration airway to thereby terminate the episode of OSA. If an episode of CSA is detected, the device could then deliver periodic stimulation signals to the diaphragm via direct electrical stimulation of the phrenic nerves to cause the diaphragm to resume a proper respiratory rhythm. This is referred to as phrenic nerve stimulation (PNS) therapy. (See, for example, U.S. Pat. No. 5,056,519 to Vince, entitled "Unilateral Diaphragmatic Pacer" and U.S. Pat. No. 6,415,183 to Scheiner, et al., entitled "Method and Apparatus for Diaphragmatic Pacing.") If apnea/hypopnea arises due to CSR, episodes of apnea occurring during CSR may be individually detected and appropriate therapy applied, such as nerve stimulation therapy similar to that used in connection with CSA. Within implantable systems lacking nerve or upper airway stimulators for directly terminating the episode of apnea, warning signals may instead be generated (either via an implanted warning device or a bedside monitor) for awakening or otherwise alerting the patient so as to cause the patient to resume normal breathing. In any case, by promptly detecting the onset of an individual episode of apnea/hypopnea, therapy or warning signals can be delivered immediately so as to allow for prompt termination of the episode of apnea/hypopnea, thus reducing the its adverse effects.

Such an implantable medical system could utilize a pacemaker or ICD for use as a controller to coordinate the detection of episodes of apnea and the delivery of therapy in response thereto. Pacemakers and ICDs are usually implanted primarily for use in applying cardiac therapy for treating cardiac arrhythmias. However, many patients who are candidates for pacemakers or ICDs also suffer from apnea and hence could benefit from additional functionality directed to the detection and treatment of apnea. Alternatively, rather than using a pacemaker or ICD, the implantable medical system could be implemented as a dedicated implantable device configured specifically for the purposes of detecting apnea/hypopnea.

Hence, it would be highly beneficial to provide techniques for detecting the onset of individual episodes of apnea/hypopnea, particularly for use within implantable medical systems. Heretofore, however, prompt and reliable detection of the onset of individual episodes of apnea/hypopnea has proven to be problematic. Even in the absence of apnea/hypopnea, respiration is often fairly infrequent (particularly while a patient is asleep) and so the lack of respiration for some period of time does not necessarily indicate the onset of apnea/hypopnea. False detection of apnea/hypopnea, when a patient is otherwise breathing properly, can result in unnecessary or improper therapy. Accordingly, to avoid such false positives, many conventional automatic apnea/hypopnea detection techniques require that little or no respiration be detected for some extended period of time—often twenty seconds or more—before an indication of apnea/hypopnea is made. By then, however, if apnea/hypopnea is indeed occurring, it has already been ongoing for some time and so prompt detection is not achieved; therefore desired therapy is delayed.

Accordingly, it would be highly desirable to provide techniques for promptly and reliably detecting the onset of individual episodes of apnea/hypopnea—preferably in real time—and it is to this end that the invention is primarily directed.

SUMMARY

In accordance with one illustrative embodiment, techniques are provided for detecting the onset of an episode of substantially reduced respiration (e.g. apnea or hypopnea) within a patient using an implantable medical system. Briefly, a moving threshold is generated based on recent respiration cycles and differences are accumulated between amplitudes of respiration cycles and the moving threshold. The onset of an episode of substantially reduced respiration is then detected based upon the accumulated differences. Preferably, the moving threshold is a short term moving average calculated based on only, for example, the last three respiration cycles or based on a similar interval of time. By exploiting the short term moving average, detection is thereby achieved substantially in real time.

The above-described technique is particularly effective for detecting episodes of frank apnea by exploiting the fact that most episodes of frank apnea are preceded by a sharp drop in respiration. Hence, by accumulating differences between new respiration amplitudes and a short term moving average of respiration amplitudes, any sharp drop in respiration amplitude can be quickly detected. Indeed, the drop in respiration amplitude can often be detected before the amplitudes of individual respiration cycles fall below some minimal threshold indicative of apnea. In other words, by the time the amplitudes of individual respiration cycles drop to levels directly indicative of apnea, the technique will already have detected the episode and, if applicable, begun delivering therapy. In this manner, apnea detection is performed substantially in real-time. The technique is, however, also applicable to detecting episodes of hypopnea, which often commence with a sharp drop in respiration.

In one example, the moving threshold is based on mean and standard deviations in the amplitudes of the last three respiration cycles. The amplitude values are derived from thoracic impedance $Z(t)$ signals. Briefly, the derivative $(dZ/dt)$ of the thoracic impedance is calculated, then individual respiration cycles are detected by identifying consecutive zero crossing points in the derivative that are associated with inspiration. The amplitude of an individual respiration cycle is then obtained by integrating the derivative of the thoracic impedance between the consecutive zero crossing points. In this manner, any drift in thoracic impedance is eliminated thereby permitting the amplitudes of individual respiration cycles to be reliably calculated. In one specific example, thoracic impedance is detected via pacing leads implanted within chambers of the heart. The thoracic impedance signal is filtered so as to eliminate changes in impedance caused by the beating of the heart. By using impedance derived from cardiac pacing leads, apnea/hypopnea can thereby be detected using a pacemaker or ICD without requiring additional leads or sensors beyond those otherwise employed in cardiac pacing. If desired, however, additional leads or sensors may be provided. For example, a blood oxygen sensor maybe implanted in a chamber of the heart to confirm the detection of apnea. In addition, in the alternative, the detection techniques of the invention may be implemented within other implantable devices besides pacemakers or ICDs, such as dedicated devices provided specifically for detecting apnea/hypopnea.

Also in one example, upon detection of the onset of an episode of apnea, the implantable medical system determines the type of apnea and delivers appropriate therapy. In this regard, if a phrenic nerve sensor is provided, the implantable system distinguishes OSA from other forms of apnea based on the presence or absence of phrenic nerve signals. More specifically, if phrenic nerve signals are present, then the episode of apnea is deemed to be OSA and appropriate therapy is delivered. For example, if the implanted system includes a nerve stimulator mounted near muscles adjacent the soft palate of throat of the patient, the nerve stimulator is then employed to stimulate the muscles to increase muscle tone sufficient to reopen the blocked respiration airway to thereby terminate the episode of OSA. However, if phrenic nerve signals are not detected, then the episode of apnea is either due to CSA or CSR. In either case, PNS therapy can then be applied to the phrenic nerves by the implanted system via a phrenic nerve stimulator, if so equipped, to stimulate breathing so as to terminate the episode of apnea. Alternatively, a muscle tone sensor in the upper airway may be used to distinguish OSA from other forms of apnea for determining the type of therapy to be delivered. Similar or alternative forms of therapy may be employed upon detection of hypopnea rather than apnea.

If nerve and upper airway stimulators are not provided, an alarm device may be triggered to alert the patient upon detection of an episode of apnea/hypopnea. The alarm device may be an implanted device or a bedside warning system. In this manner, if the patient is asleep, the patient is thereby awakened so as to prevent extended episodes of apnea/hypopnea from occurring, which can cause significant variances in blood chemistry that can exacerbate other medical conditions such as CHF. In addition, once a determination has been made by the implanted system that the patient is subject to frequent episodes of apnea/hypopnea, dynamic atrial overdrive (DAO) pacing may be delivered in an effort to prevent additional episodes from occurring. If an implantable drug pump is provided, the implanted system may be programmed to selectively deliver medications deemed effective in addressing apnea/hypopnea. In addition, regardless of the type of therapy, diagnostic information representative of any episodes of apnea/hypopnea is preferably recorded within a memory of the implanted system for subsequent review by a physician.

Hence, techniques are provided for detecting the onset of an episode of significantly reduced respiration substantially in real-time and for initiating appropriate therapy.

BRIEF DESCRIPTION OF THE DRAWINGS

The above and further features, advantages and benefits will be apparent upon consideration of the descriptions herein taken in conjunction with the accompanying drawings, in which:

FIG. 8 is a graph illustrating exemplary filtered thoracic impedance signals and respiration amplitudes derived therefrom via the method of FIG. 7;

DETAILED DESCRIPTION OF THE PREFERRED EMBODIMENTS

The following description includes the best mode presently contemplated. This description is not to be taken in a limiting sense but is made merely to describe general principles of the illustrative embodiments. The scope of the invention should be ascertained with reference to the issued claims. In the description that follows, like numerals or reference designators are used to refer to like parts or elements throughout.

Overview of Implantable Apnea/Hypopnea Responsive System

Figure 1:
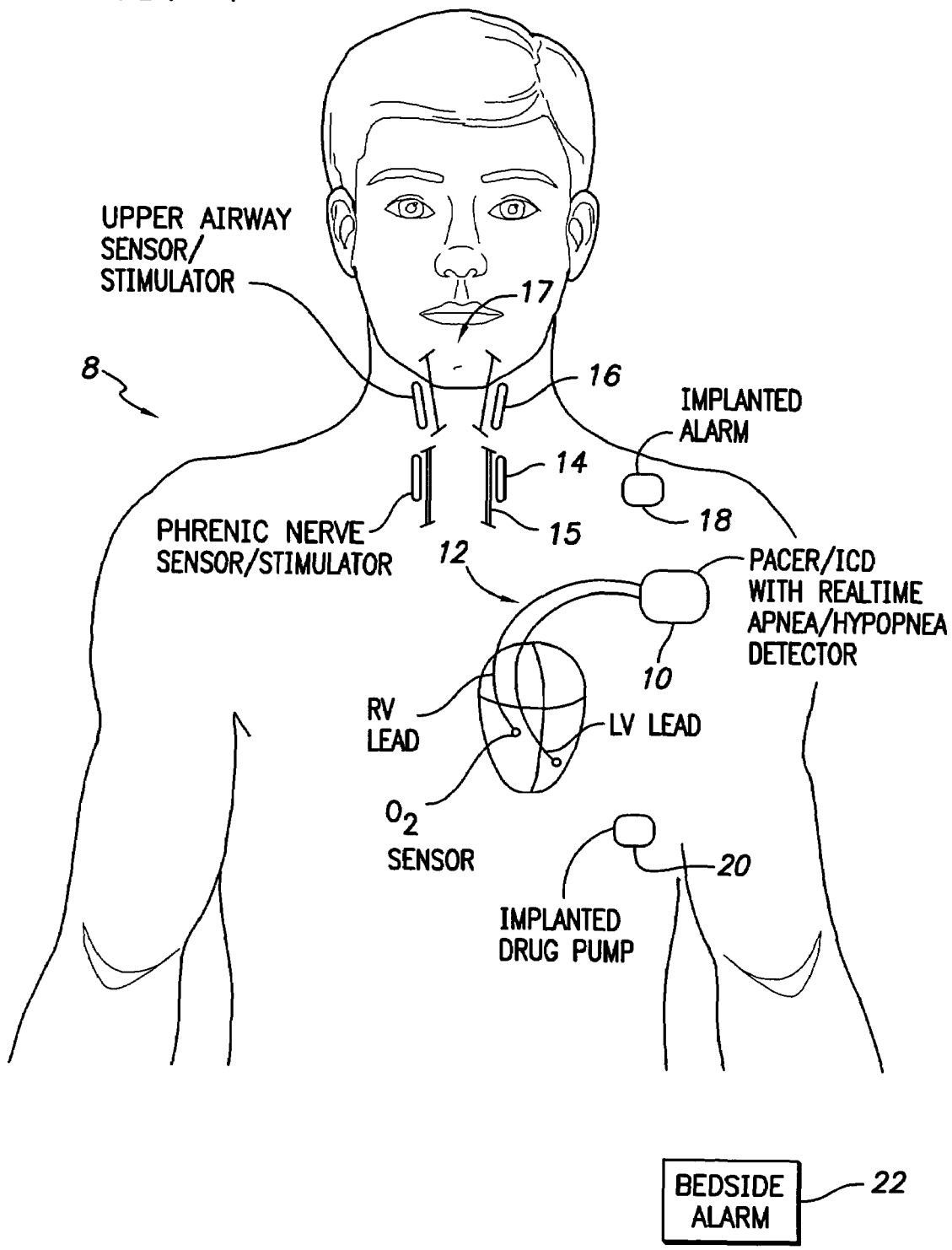
FIG. 1 illustrates pertinent components of an implantable apnea/hypopnea responsive medical system having a pacer/ICD capable of detecting an episode of substantially reduced respiration (i.e. apnea/hypopnea) based on thoracic impedance signals detected via leads mounted in the heart (only two of which are shown) and having additional implanted components for delivering therapy or warning signals in response thereto.
Figure 4:
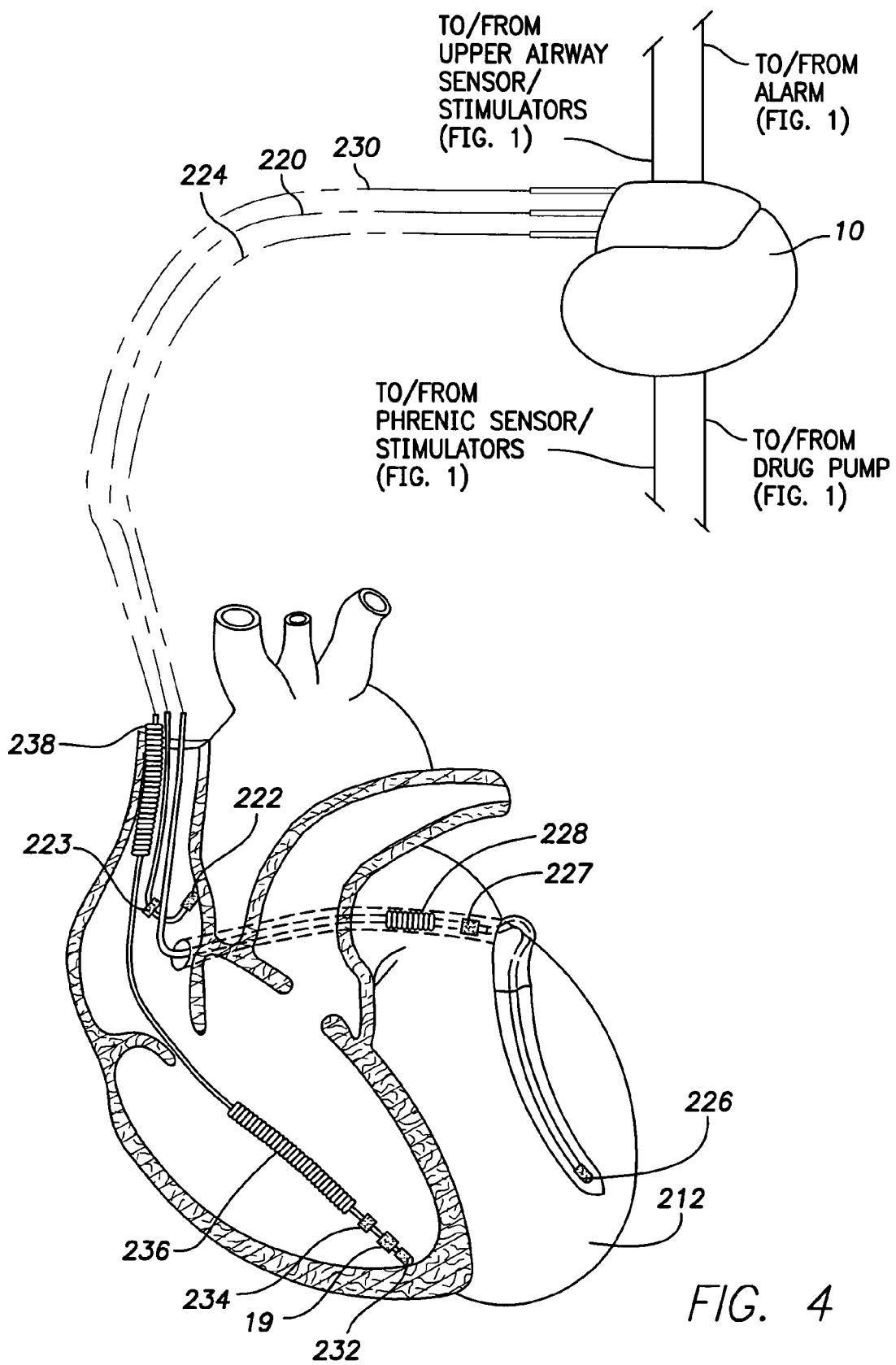
FIG. 4 is a simplified, partly cutaway view, illustrating the pacer/ICD of FIG. 1 along with a complete set of leads implanted in the heart of a patient.

FIG. 1 illustrates an implantable apnea/hypopnea responsive medical system 8 capable of detecting individual episodes of substantially reduced respiration and delivering appropriate therapy. Apnea/hypopnea responsive system 8 includes a pacer/ICD 10 or other cardiac stimulation device that incorporates internal components (shown in FIGS. 5 and 6) for detecting apnea/hypopnea and controlling delivery of therapy in response thereto. To this end, pacer/ICD 10 receives impedance signals from various cardiac pacing leads—two of which (left and right ventricular pacing leads 12)—are shown in FIG. 1. A complete set of exemplary pacing leads are shown in FIG. 4. Based on the received impedance signals, the pacer/ICD detects episodes of apnea/hypopnea using a real-time technique summarized below with reference to FIG. 2. Although a pacer/ICD is illustrated in FIG. 1, it should be understood that the detection techniques of the invention may be implemented within other implantable devices, particularly including dedicated detection devices not capable of cardiac stimulation therapy.

Once apnea/hypopnea has been detected, the system uses additional components (if so equipped) to identify the type of apnea/hypopnea and to deliver appropriate therapy. To this end, if apnea is detected, the system distinguishes among OSA, CSA and apnea arising due to CSR based, in part, on the presence or absence of phrenic nerve signals detected by phrenic nerve sensor/stimulators 14. The phrenic nerve signals are sensed from left and right phrenic nerves 15. If phrenic nerve signals are instead present, then the episode of apnea is deemed to be an episode of OSA. If so, the pacer/ICD controls a set of upper airway stimulators 16, implanted near the soft palate region of the throat surrounding respiratory airway 17 to stimulate adjacent muscles to increase muscle tone and expand the airway, thus alleviating airway blockage associated with OSA. If phrenic nerve signals are instead absent, then the episode of apnea is deemed to be due to CSA or CSR. In either case, the pacer/ICD controls phrenic nerve sensor/stimulators 14 to apply PNS to rhythmically stimulate the diaphragm to cause the diaphragm to contract, thus triggering breathing. Additionally, if so required, CSA can be distinguished from CSR based on an analysis of recent breathing patterns. If the patterns indicate cyclic variations between periods of hyperpnea and hypopnea, then the episode of apnea is likely due to CSR; otherwise CSA. Additionally, or in the alternative, the upper airway stimulators provided near the upper airway may be equipped with sensors for sensing muscle tone for the purposes of distinguishing OSA from non-obstructive forms of apnea. Upper airway sensors for detecting OSA are discussed in U.S. Pat. No. 5,146,918, to Kallok, et al., entitled "Demand Apnea Control of Central and Obstructive Sleep Apnea." Additionally, an oxygen sensor 19 may be implanted within a chamber of the heart for confirming the detection of apnea/hypopnea made based on an analysis of the impedance signals. The oxygen sensor may also be used to determine when to terminate any therapy being applied. In the example of FIG. 1, the oxygen sensor is mounted on the RV lead near its distal end. This is merely exemplary. Oxygen sensors for implant within the heart are discussed in U.S. Pat. No. 5,275,171 to Barcel, entitled "Implantable Lead and Sensor".

If stimulators are not provided near the upper airway or near the phrenic nerves then, upon detection of an episode of apnea/hypopnea, the pacer/ICD instead activates an internal apnea/hypopnea alarm 18 or an external bedside alarm 22. Internal alarm 18 may be a vibrating device or a "tickle" voltage device that, in either case, provides perceptible stimulation to the patient to alert or awaken the patient so as to terminate the episode of apnea/hypopnea. The bedside alarm may provide audible or visual alarm signals of sufficient magnitude to alert or awaken the patient. Additionally, or in the alternative, the system may include a drug pump 20 capable of the delivering drug therapy in an attempt to prevent the onset of additional episodes of apnea/hypopnea. Discussions of possible medications for preventing the onset of apnea/hypopnea are provided below. In addition, the pacer/ICD may be used to deliver overdrive pacing for the purposes of preventing additional episodes of apnea/hypopnea from occurring. In one example, upon the detection of initial episodes of apnea/hypopnea, overdrive pacing and/or drug therapy is delivered to the patient in an attempt to prevent the onset of additional episodes of apnea/hypopnea. If additional episodes nevertheless occur and the system is not equipped with stimulators for directly terminating the apnea/hypopnea, then alarm signals are generated to alert or awaken the patient. Implantable upper airway muscle stimulators and phrenic nerve stimulators are preferable within patients suffering from chronic apnea/hypopnea to allow individual episodes of apnea/hypopnea to be terminated without needing to repeatedly alert or awaken the patient. If an activity sensor is provided within the pacer/ICD, the form of the alarm may be controlled based on patient activity. For example, if the activity level indicates that the patient is asleep, a more noticeable alarm may be employed than if the patient is deemed to be awake. In addition, while the patient is asleep, the intensity of the alarm signal can be periodically increased until the patient awakens, as detected by the activity sensor.

Thus, FIG. 1 provides an overview of an implantable system for detecting apnea/hypopnea and for delivering therapy in response thereto. Internal signal transmission lines for interconnecting the various implanted components are not shown. Alternatively, wireless signal transmission may be employed. In addition, it should be appreciated that systems provided in accordance with invention need not include all the components shown in FIG. 1. In many cases, for example, the system will include only the pacer/ICD and its leads. All therapy will be in the form of overdrive pacing. Other implementations will employ muscle and phrenic nerve stimulators, but no internal or external alarms and no drug pumps. Still other implementations may employ additional components, such as additional muscle stimulators for directly stimulating the intercostal chest muscles associated with respiration. Also, note that the particular locations of the implanted components are merely exemplary. Phrenic nerve signals can typically be sensed at any point along the phrenic nerves. Since the phrenic nerves pass along the sides of the heart, it may be expedient to sense phrenic nerve signals using epicardial sensors mounted adjacent the phrenic nerves on the heart. These are just a few exemplary embodiments. No attempt is made herein to describe all possible combinations of components that may be provided in accordance with the general principles of the invention.

Overview of Technique For Detecting Episodes of Reduced Respiration

Figure 2:
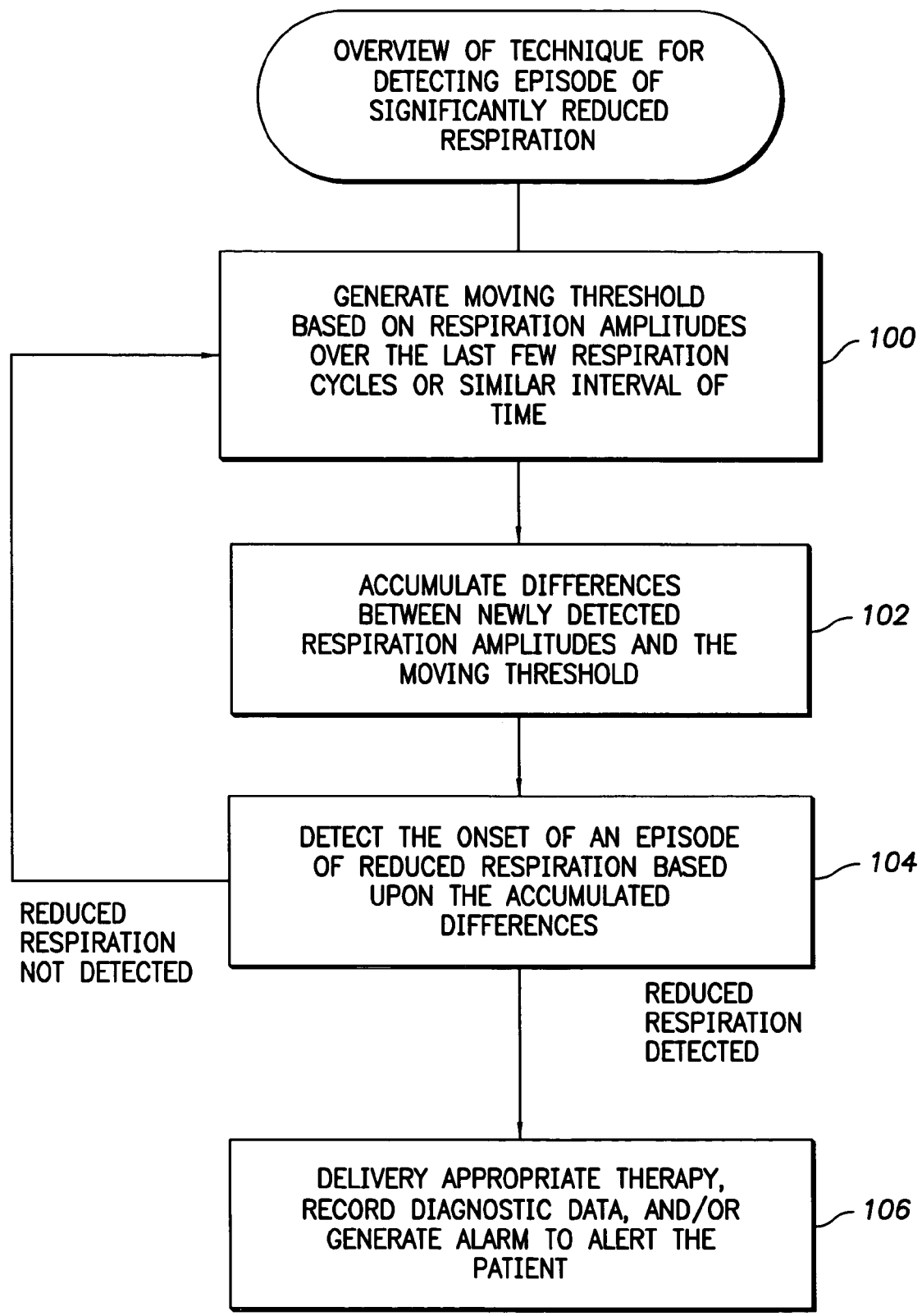
FIG. 2 is a flow diagram providing an overview of a method for detecting the onset of an episode of substantially reduced respiration performed by the system of FIG. 1.

FIG. 2 provides an overview of the techniques of the invention for detecting episodes of significantly reduced respiration, i.e. apnea or hypopnea. Initially, at step 100, the implantable pacer/ICD or other implantable device generates a moving threshold based on respiration amplitudes detected over the last few respiration cycles—preferably only the last three respiration cycles—or over a similar interval of time. The interval of time may be set, for example, based on the current respiration rate to be equal to about three respiration cycles. At step 102, the pacer/ICD accumulates differences between newly detected respiration amplitudes and the moving threshold. Then, at step 104, the onset of an episode of reduced respiration is detected based upon the accumulated differences. In one example, which will be described in greater detail below with reference to FIGS. 7-10, differences between newly detected respiration amplitudes and the moving threshold are only accumulated only so long as consecutive respiration amplitudes each fall below the moving threshold. The onset of an episode of reduced respiration is identified once the accumulated differences exceed a fixed detection threshold. In another example, which will be described in greater detail below with reference to FIGS. 12 and 13, differences are accumulated at all times and are compared against two thresholds—one indicating the onset of an episode of reduced respiration and the other indicating the end of the episode. Depending upon the implementation, different thresholds may be employed for specifically detecting hypopnea as opposed to apnea. In any case, assuming an episode of reduced respiration is detected then, at step 106, appropriate therapy is delivered, diagnostic information is recorded, and/or warning signals are generated to alert or awaken the patient.

The use of the moving threshold in the first example (wherein differences between newly detected respiration amplitudes and the moving threshold are only accumulated only so long as consecutive respiration amplitudes each fall below the moving threshold) is shown by way of three respiration patterns in FIG. 3. Initially, a normal respiration pattern 108 is shown, wherein the moving threshold remains more or less constant. In this example, moving threshold 109 remains below the amplitude of the normal respiration cycles and so differences in the amplitudes of the respiration cycles and the moving threshold are not accumulated, reduced respiration is not detected and no therapy is delivered. Next, a brief period of slightly reduced respiration insufficient to trigger therapy is illustrated by way of respiration pattern 110. Here, the respiration amplitudes of two consecutive respiration cycles fall below the moving threshold. Accordingly, the pacer/ICD begins to calculate the accumulated deficit 114, i.e. the difference between the moving threshold 109 and the amplitudes of the individual respiration cycles, for comparison against a detection threshold 116. The accumulation of the deficit is terminated once a respiration cycle (cycle 117) exceeds moving threshold 109. At no point in this example does the accumulated deficit 114 exceed fixed detection threshold 116 and so no therapy is delivered. In a final example, shown by way of respiration pattern 118, individual respiration patterns remain below the moving threshold 109 sufficiently long so that accumulated deficit 120 exceeds fixed detection threshold 116 and so an episode of reduced respiration is detected and therapy is initiated.

Figure 3:
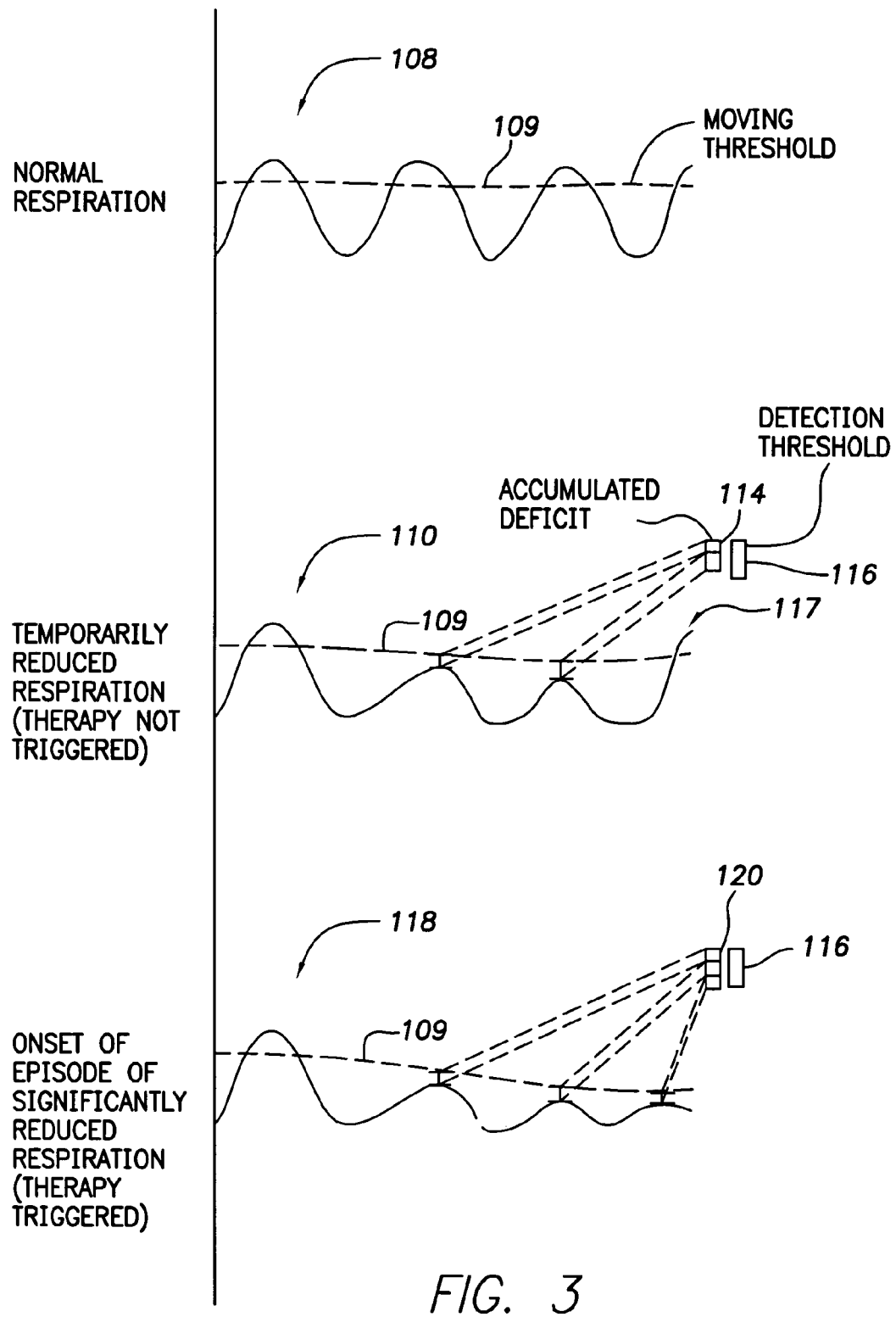
FIG. 3 is a graph illustrating exemplary, stylized respiration patterns analyzed via the method of FIG. 2.

Hence, FIG. 3 illustrates exemplary respiration patterns analyzed via the technique of FIG. 2 wherein differences are accumulated between respiration amplitudes and a moving threshold for use in detecting onset of an episode of reduced respiration. By accumulating deficits in this manner, any sharp drop in respiration amplitude is thereby promptly detected. As noted above, episodes of hypopnea usually commence with a sharp drop in respiration amplitude and episodes of apnea are usually preceded by a sharp drop in respiration amplitude. So by detecting and quantifying the drop in amplitude for comparison against a moving threshold, an episode of apnea or hypopnea can be detected even before individual respiration amplitudes fall below some minimal threshold indicative of apnea or hypopnea. In other words, by detecting the drop in respiration amplitude rather than by examining individual respiration amplitudes, the onset of an episode of apnea/hypopnea can be detected substantially in real-time so that therapy can be promptly initiated. One advantage of using dz/dt and its accumulation is there is no need to store all waveform for post-processing.

Note that, in the example of FIG. 3, the numerical difference between the peak amplitude of the respiration cycle and the moving threshold is exploited. This is shown for illustrative purposes only. Preferably, the amplitudes of respiration cycles are instead obtained by integrating the derivative of thoracic impedance signals over inspiration portions of each respiration cycle, in a manner to be described in greater detail below.

Thus, FIGS. 1-3 provide an overview of the detection techniques of the invention. The techniques of the invention can be implemented in a wide range of embodiments and FIGS. 1-3 are intended to provide only an overview. Detailed exemplary implementations are described below.

Pacemaker/ICD

Figure 5:
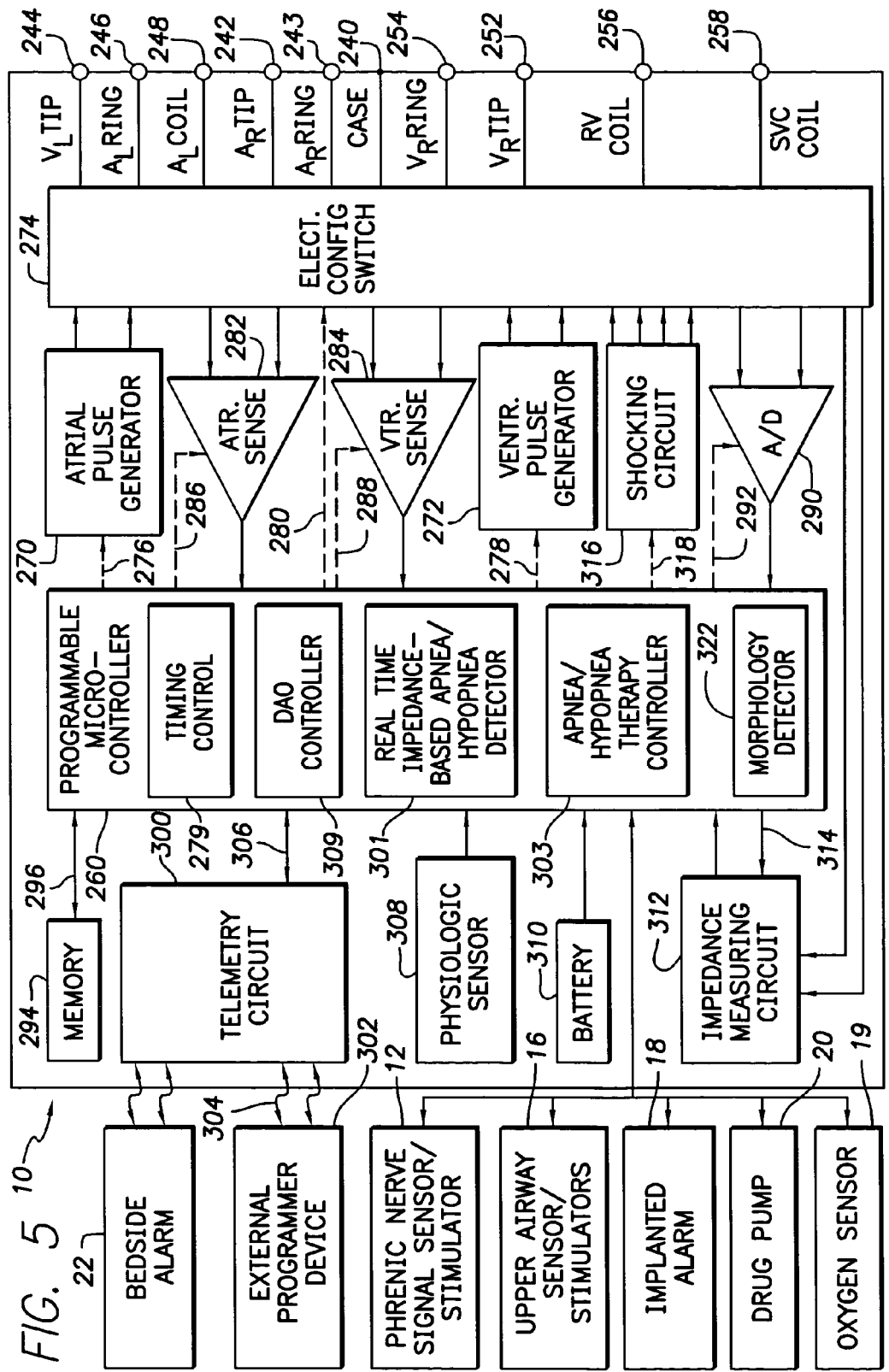
FIG. 5 is a functional block diagram of the pacer/ICD of FIG. 4, illustrating basic circuit elements that provide cardioversion, defibrillation and/or pacing stimulation in four chambers of the heart and particularly illustrating a real-time impedance-based apnea/hypopnea detector for detecting apnea/hypopnea based on thoracic impedance signals and an apnea/hypopnea therapy controller for controlling delivery of therapy in response thereto.

With reference to FIGS. 4 and 5, a detailed description of the pacer/ICD of FIG. 1 will now be provided. More specifically, FIG. 4 provides a block diagram of an exemplary dual-chamber stimulation device capable of treating both fast and slow arrhythmias with stimulation therapy, including cardioversion, defibrillation, and pacing stimulation, as well as capable of detecting apnea/hypopnea and controlling delivering of therapy in response thereto.

To provide atrial chamber pacing stimulation and sensing, pacer/ICD 10 is shown in electrical communication with a heart 212 by way of a left atrial lead 220 having an atrial tip electrode 222 and an atrial ring electrode 223 implanted in the atrial appendage. Pacer/ICD 10 is also in electrical communication with the heart by way of a right ventricular lead 230 having, in this embodiment, a ventricular tip electrode 232, a right ventricular ring electrode 234, a right ventricular (RV) coil electrode 236, and a superior vena cava (SVC) coil electrode 238. Typically, the right ventricular lead 230 is transvenously inserted into the heart so as to place the RV coil electrode 236 in the right ventricular apex, and the SVC coil electrode 238 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 224 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228. With this configuration, biventricular pacing can be performed. Although only three leads are shown in FIG. 4, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 5. While a particular pacer/

ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea/hypopnea detection and therapy.

The housing 240 for pacer/ICD 10, shown schematically in FIG. 5, is often referred to as the "can", "case" or "case electrode" and may be programmably selected to act as the return electrode for all "unipolar" modes. The housing 240 may further be used as a return electrode alone or in combination with one or more of the coil electrodes, 228, 236 and 238, for shocking purposes. The housing 240 further includes a connector (not shown) having a plurality of terminals, 242, 243, 244, 246, 248, 252, 254, 256 and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 222 and a right atrial ring ($A_R$ RING) electrode 243 adapted for connection to right atrial ring electrode 223. To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular ring electrode 226, the left atrial tip electrode 227, and the left atrial coil electrode 228, respectively. To support right chamber sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 232, right ventricular ring electrode 234, the RV coil electrode 236, and the SVC coil electrode 238, respectively. Blood oxygen sensor 19 (FIG. 1) is also shown.

At the core of pacer/ICD 10 is a programmable microcontroller 260, which controls the various modes of stimulation therapy. As is well known in the art, the microcontroller 260 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design and operation of the microcontroller 260 are not critical to the invention. Rather, any suitable microcontroller 260 may be used that carries out the functions described herein. The use of microprocessor-based control circuits for performing timing and data analysis functions are well known in the art.

As shown in FIG. 5, an atrial pulse generator 270 and a ventricular pulse generator 272 generate pacing stimulation pulses for delivery by the right atrial lead 220, the right ventricular lead 230, and/or the coronary sinus lead 224 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 282 and ventricular sensing circuits 284 may also be selectively coupled to the right atrial lead 220, coronary sinus lead 224, and the right ventricular lead 230, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers or shared amplifiers. The switch 274 determines the "sensing polarity" of the cardiac signal by selectively closing the appropriate switches, as is also known in the art. In this way, the clinician may program the sensing polarity independent of the stimulation polarity. Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity in the appropriate chambers of the heart.

For arrhythmia detection, pacer/ICD 10 utilizes the atrial and ventricular sensing circuits, 282 and 284, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 260 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 302. The data acquisition system 290 is coupled to the right atrial lead 220, the coronary sinus lead 224, and the right ventricular lead 230 through the switch 274 to sample cardiac signals across any pair of desired electrodes. The microcontroller 260 is further coupled to a memory 294 by a suitable data/address bus 296, wherein the programmable operating parameters used by the microcontroller 260 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 294 through a telemetry circuit 300 in telemetric communication with the external device 302, such as a programmer, transtelephonic transceiver or a diagnostic system analyzer. The telemetry circuit 300 is activated by the microcontroller by a control signal 306. The telemetry circuit 300 advantageously allows intracardiac electrograms and status information relating to the operation of pacer/ICD 10 (as contained in the microcontroller 260 or memory 294) to be sent to the external device 302 through an established communication link 304. In the preferred embodiment, pacer/ICD 10 further includes a physiologic sensor 308, commonly referred to as a "rate-responsive" sensor because it is typically used to adjust pacing stimulation rate according to the exercise state of the patient. However, the physiological sensor 308 may further be used to detect changes in cardiac output, changes in the physiological condition of the heart, or diurnal changes in activity (e.g., detecting sleep and wake states). Accordingly, the microcontroller 260 responds by adjusting the various pacing parameters (such as rate, AV Delay, V-V Delay, etc.) at which the atrial and ventricular pulse generators, 270 and 272, generate stimulation pulses. While shown as being included within pacer/ICD 10, it is to be understood that the physiologic sensor 308 may also be external to pacer/ICD 10, yet still be implanted within or carried by the patient. A common type of rate responsive sensor is an activity sensor, such as an accelerometer or a piezoelectric crystal, which is mounted within the housing 240 of pacer/ICD 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The pacer/ICD additionally includes a battery 310, which provides operating power to all of the circuits shown in FIG. 5. The battery 310 may vary depending on the capabilities of pacer/ICD 10. If the system only provides low voltage therapy, a lithium iodine or lithium copper fluoride cell may be utilized. For pacer/ICD 10, which employs shocking therapy, the battery 310 must be capable of operating at low current drains for long periods, and then be capable of providing high-current pulses (for capacitor charging) when the patient requires a shock pulse. The battery 310 must also have a predictable discharge characteristic so that elective replacement time can be detected. Accordingly, pacer/ICD 10 is preferably capable of high voltage therapy and employs lithium/silver vanadium oxide batteries, as is true for most (if not all) current devices. As further shown in FIG. 5, pacer/ICD 10 is shown as having an impedance measuring circuit 312 which is enabled by the microcontroller 260 via a control signal 314. Here, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 260 further controls a shocking circuit 316 by way of a control signal 318. The shocking circuit 316 generates shocking pulses of low (up to 0.5 joules), moderate (0.5-10 joules) or high energy (11 to 40 joules), as controlled by the microcontroller 260. Such shocking pulses are applied to the heart of the patient through at least two shocking electrodes, and as shown in this embodiment, selected from the left atrial coil electrode 228, the RV coil electrode 236, and/or the SVC coil electrode 238. The housing 240 may act as an active electrode in combination with the RV electrode 236, or as part of a split electrical vector using the SVC coil electrode 238 or the left atrial coil electrode 228 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 260 is capable of controlling the synchronous or asynchronous delivery of the shocking pulses.

Microcontroller 260 also includes the following components directed to the detection and treatment of apnea/hypopnea. A real-time impedance-based detector 301 detects apnea/hypopnea based upon the aforementioned accumulated deficits. In response to individual detected episodes of, apnea/hypopnea therapy controller 303 controls implanted alarm 18 or bedside alarm 22 to deliver appropriate alarm signals to alert or awaken the patient for terminating the episode of apnea/hypopnea. In addition, as noted above with reference to FIG. 1, phrenic nerve sensor/simulators 12 (if provided) are activated during episodes of CSA or CSR to generate nerve signals to simulate breathing. Upper airway stimulators 16 (if provided) are activated during episodes of OSA to improve muscle tone around the respiratory airway so as to alleviate any blockage. If the patient is found to suffer from chronic apnea/hypopnea, overdrive pacing is delivered in attempt to prevent the onset of additional episodes of apnea/hypopnea using DAO controller 309. In addition, implantable drug pump 20 (if provided) is activated to deliver medications appropriate for the treatment of apnea/hypopnea.

The operation of the real-time impedance-based detector and the apnea/hypopnea therapy controller will be described in detail below with reference to FIG. 6. Note that, although these components are shown as being sub-components of the microcontroller, the components may be instead implemented separately from the microcontroller.

Apnea/Hypopnea Detector and Therapy Controller

Figure 6:
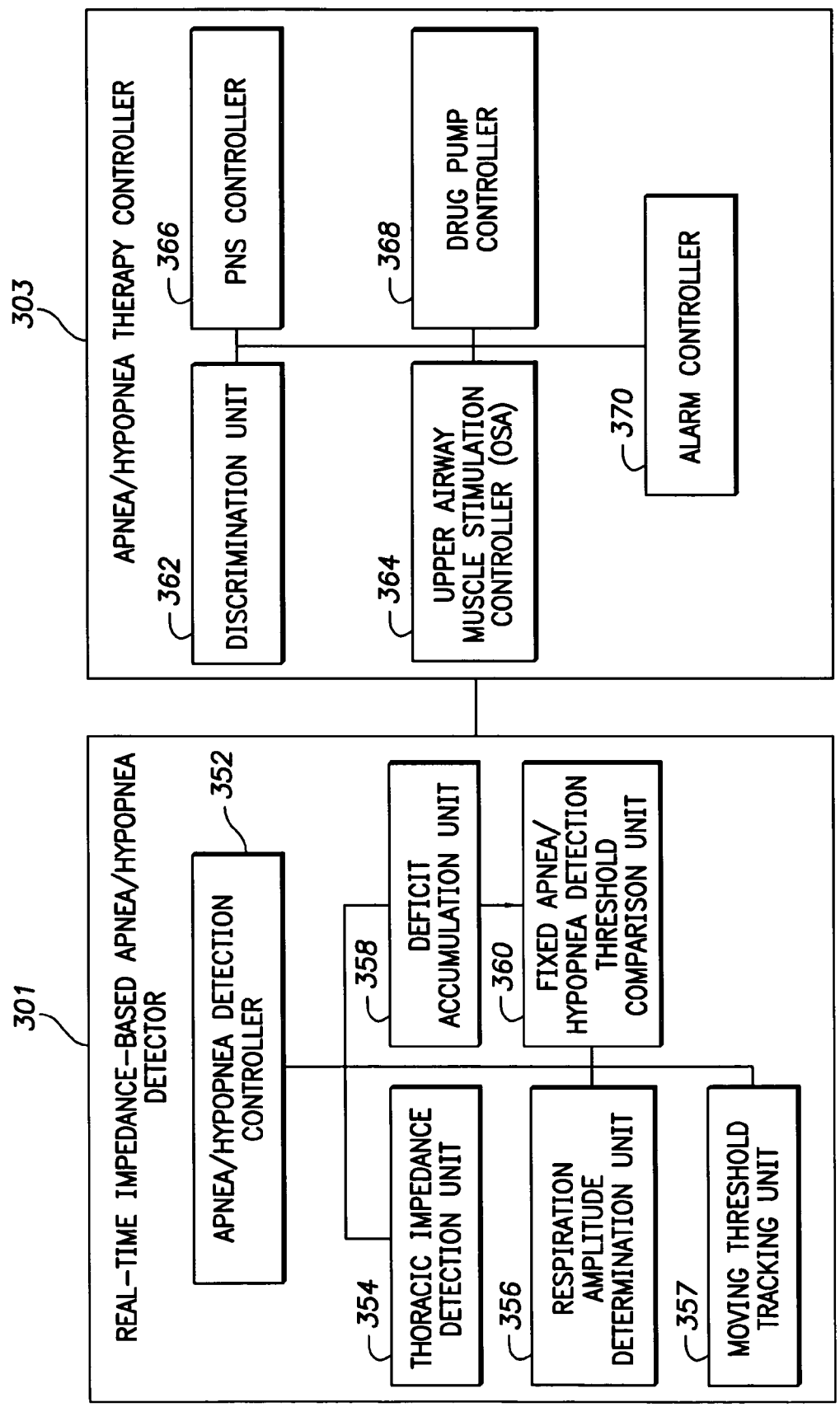
FIG. 6 is a functional block diagram of selected components of the real-time impedance-based apnea/hypopnea detector and the apnea/hypopnea therapy controller of FIG. 5.
Figure 7:
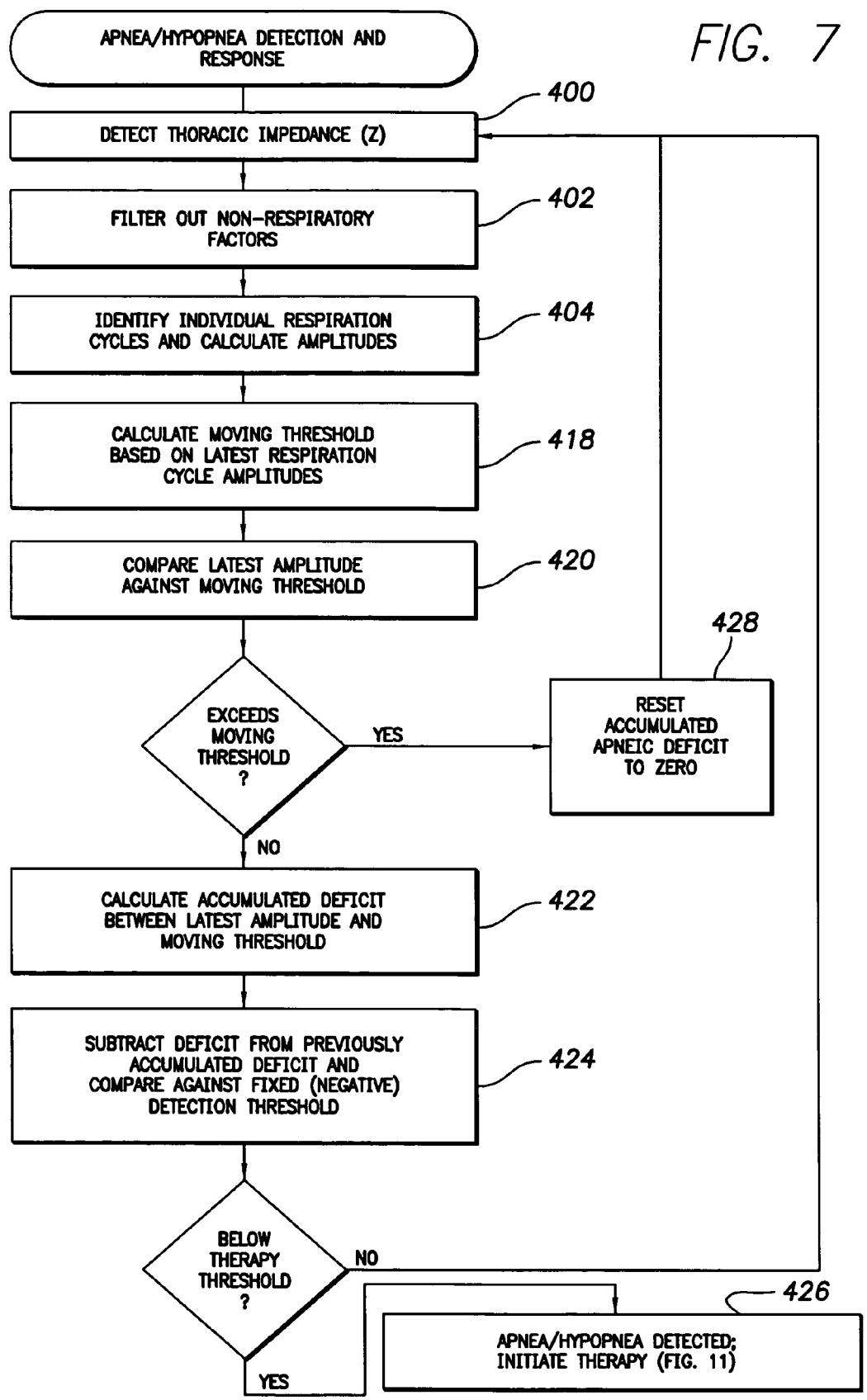
FIG. 7 is a flow diagram illustrating an exemplary method performed by the system of FIGS. 4-6 for detecting apnea/hypopnea.

Pertinent internal functional components of apnea/hypopnea detector 301 and apnea/hypopnea therapy controller 303, respectively, are shown in FIG. 6. Within detector 301, an apnea/hypopnea detection controller 352 coordinates the detection of apnea/hypopnea. To this end, a thoracic impedance detection unit 354 is controlled to detect thoracic impedance signals using selected combinations of leads shown in FIG. 4. Impedance may be detected, for example, between the two tip electrodes of the left and right ventricles. The thoracic impedance signals are filtered to eliminate the effects on thoracic impedance caused by the heart beating and other non-respiratory factors. Based on the thoracic impedance, a respiration amplitude determination unit 356 evaluates the amplitude of individual respiration cycles. Then, based upon the respiration amplitudes of the last three cycles (or over a similar interval of time), a moving threshold tracking unit 357 calculates the current value for the moving threshold. A deficit accumulation unit 358 selectively accumulates differences between new respiration amplitudes and the moving threshold. In one example, the deficit is accumulated only so long as consecutive respiration cycles all fall below the moving threshold. In another example, the deficits are accumulated at all times and compared against dual thresholds. In any case, actual comparison of the accumulated deficit against one or more thresholds is performed by a fixed apnea/hypopnea detection threshold comparison unit 360 so as to detect the onset of episode of apnea/hypopnea and, depending upon implementation, to also detect the end of the episode of apnea/hypopnea.

Once an episode of apnea/hypopnea has been detected, therapy controller 303 is activated to identify the type of apnea/hypopnea and to deliver appropriate therapy. To this end, therapy controller 303 includes a discrimination unit 362 determines whether the episode of apnea/hypopnea is due to, for example, OSA, CSA or CSR. If OSA, upper airway muscle stimulation controller 364 controls upper airway stimulators 16 (of FIG. 1) to stimulate muscles in the vicinity of the soft palate region of the throat of the patient. If CSA or CSR, then a PNS controller 366 is activated to selectively simulate the diaphragm so as to simulate breathing using phrenic nerve sensor/simulators 14 (also FIG. 1). Additionally, or in the alternative, a drug pump controller 368 is activated to control the delivery of medications via implanted drug pump 20 (also FIG. 1). Also, the DAO controller 309 (FIG. 5) can be activated to deliver overdrive pacing therapy in an effort to prevent additional episodes of apnea/hypopnea from occurring. Therapy controller 303 also includes an alarm controller 370 for controlling the generation of warning signals via implanted alarm 18 (FIG. 1) or bedside alarm 22 (also FIG. 1.) The various separate components of the therapy controller are shown in FIG. 6 for the sake of completeness. In some implementations, however, many of the individual components are not provided. For example, if upper airway stimulators are not provided, then controller 364 is not required. If a phrenic nerve stimulator is not provided, then controller 366 is not required.

Hence, FIG. 6 illustrates exemplary internal functional components of the apnea/hypopnea detector and therapy controller. Depending upon the implementation, the various components may be implemented as separate software modules. However, the modules may be combined so as to permit single modules to perform multiple functions.

Exemplary Detection and Response Technique with Single Detection Threshold

One particular example of an apnea/hypopnea detection and response technique that may be performed using the systems described above is set forth in FIGS. 7-10. At step 400 of FIG. 7, the pacer/ICD begins detecting thoracic impedance values (Z). Thoracic impedance may be detected using any of a variety of otherwise conventional techniques. An example is set forth the U.S. Pat. No. 5,817,135 to Cooper, et al., entitled "Rate-Responsive Pacemaker with Noise-Rejecting Minute Volume Determination". At step 402, the thoracic impedance values are filtered to eliminate variations in impedance caused by the beating of the heart or other non-respiration factors. In one example, a low pass filter is employed having a cutoff frequency set to some value greater than the frequency of respiratory breathing but less than the frequency associated with the beating heart. For example, a cutoff frequency of 30 cycles per minute may be employed. Then, at step 404, individual respiration cycles are identified and their individual amplitudes are calculated.

FIG. 8 illustrates a filtered version of a thoracic impedance signal by way of graph 406. As can be seen, despite filtering, there is significant drift in the impedance signal. Accordingly, to calculate the amplitudes of individual respiration cycles, the pacer/ICD first calculates the derivative of the impedance signals at each point, which is shown in FIG. 8 by way of graph 408. As can be seen, the overall drift in impedance is substantially eliminated. Then, the pacer/ICD identifies zero crossing points within the derivative of the impedance signal, which represent peaks and valleys in the actual impedance signal. Between each pair of consecutive zero crossing points corresponding to a transition from a valley to a peak, the pacer/ICD sums or integrates the derivative of the impedance signal to obtain a single amplitude value for the respiration cycle. Individual resulting amplitude values are shown in FIG. 8 by way of graph 410.

Figure 9:
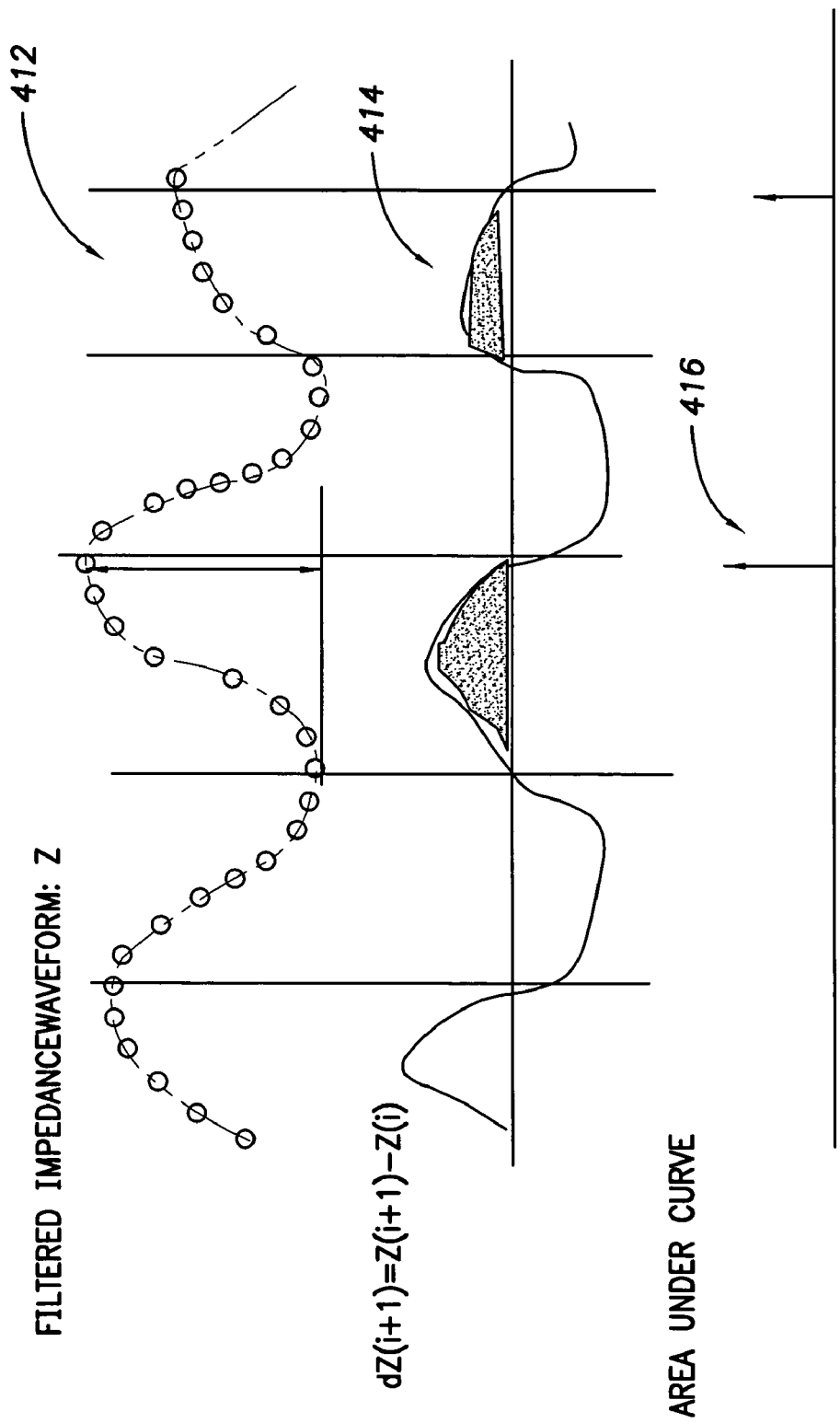
FIG. 9 is a graph illustrating exemplary filtered thoracic impedance signals for two individual respiration cycles and particularly illustrating a technique for deriving the amplitude of the respiration cycles via the method of FIG. 7.

This procedure is further illustrated in FIG. 9, which shows only a small segment 412 of the filtered impedance signal 406 of FIG. 8, and identified individual discrete values of the filtered impedance. FIG. 9 also shows the corresponding derivative of the impedance signal 414, obtained by calculating $dZ/dt(i+1)=Z(i+1)-Z(i)$, where "I" identifies individual discrete values of the filtered impedance signal. The areas under the derivative between consecutive zero crossing points (corresponding to transitions from valleys to peaks) are shaded. These shaded areas are calculated to determine the amplitude associated with the respiration cycle. Individual corresponding amplitude values are shown in FIG. 9 by way of vertical arrows 416.

Returning to FIG. 7, the pacer/ICD then calculates a moving threshold based upon the most recent respiration cycles, at step 418. More specifically, the moving threshold is calculated based upon mean and standard deviation values of the three most recent respiration cycle amplitudes. An algorithm for calculating the moving threshold is as follows:

```
z0=0;z1=0; z2=0; % 0 is the most recent
whenever new Z detected
{
    timer_tick= 6 sec
        meanz0= 0.6 *meanz1+0.4*mean(z0,z1,z2);
        stdz0= 0.6* stdz1 + 0.4* std(z0,z1,z2);
        thz0 = (meanz0 + stdz0 ) /2;
    meanz1= meanz0;
        stdz1 = stdz0;
}
Timer_ISR( ) // CPU interrupt driven routine
```

```
{
    timer_tick --;
    If timer_tick =0, measure Z and pass to above routine
}
```

In this algorithm, "thz0" represents the moving threshold that is being calculated. As can be seen, thz0 is set based on a combination of meanz0 and stdz0, which are mean and standard deviation values generated based on Z. Other algorithms for defining the moving threshold may instead be used. Also note that, in some cases, because respiration amplitude has dropped substantially to zero, the amplitude for a given respiration cycle will be difficult to obtain because zero crossing points in the derivative of the impedance value will be difficult to identify. Accordingly, if the pacer/ICD is unable to identify a respiration cycle within a programmable period of, typically, six seconds, the pacer/ICD measures the current impedance Z then uses that value of Z to update the threshold. This is indicated in the aforementioned algorithm by way of the timer subroutine. By using the timer subroutine, it is assured that the system does not wait indefinitely to detect a next respiration cycle in circumstances where respiration is substantially nonexistent.

Once the moving threshold (thz0) has been calculated, the amplitude of the most recent respiration cycle is compared, at step 420, against the moving threshold. Any suitable technique may be employed for comparing the amplitude of the most recent respiration cycle to the moving threshold (thz0). If the latest amplitude is below the moving threshold, then step 422 is performed wherein the pacer/ICD calculates the deficit between the latest amplitude and the current value of the moving threshold. This new accumulated deficit value is subtracted from previously accumulated deficit values, at step 424, for comparison against a fixed (negative) apnea/hypopnea detection threshold. If the accumulated deficit drops below the fixed negative detection threshold, then apnea/hypopnea is thereby detected and therapy is initiated, at step 426. So long as the accumulated deficit remains above the fixed negative threshold, steps 400-424 are repeated. Note that if the amplitude of any individual respiration amplitude value exceeds the current moving threshold (thz0) following step 420, then step 428 is instead performed wherein the accumulated deficit value is reset to zero.

Figure 10:
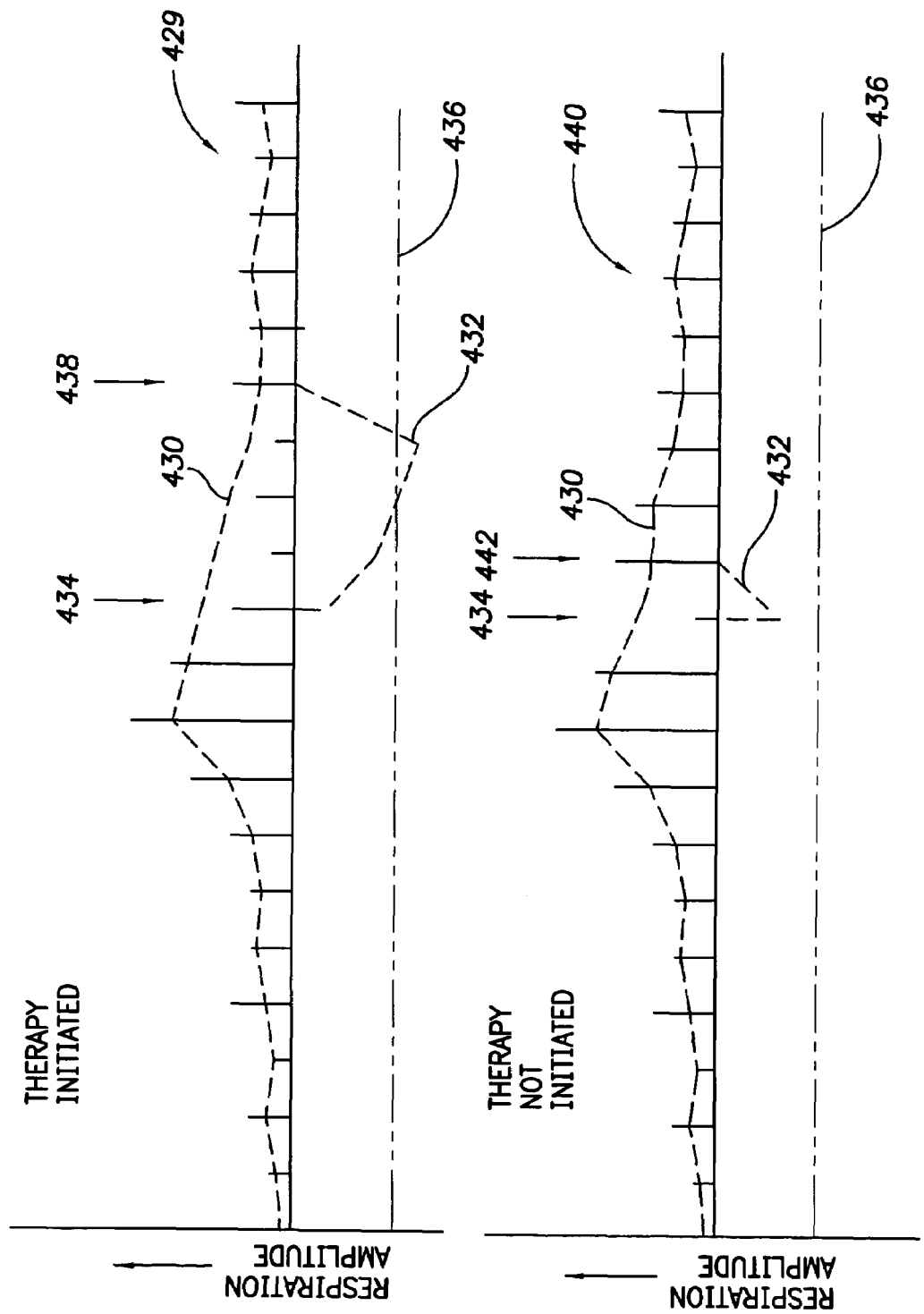
FIG. 10 is a graph illustrating exemplary respiration amplitude values, moving threshold values and an accumulated deficit between the respiration amplitudes and the moving threshold obtained via the method of FIG. 7.

This procedure is illustrated by way of the examples of FIG. 10. Briefly, a first graph of FIG. 10 illustrates a set of individual amplitude values 429 calculated using the aforementioned techniques. The moving threshold is shown by way of dotted line 430. The accumulated deficit is shown by way of dashed line 432. In this example, the deficit is represented by a negative number. The amplitude of the respiration cycle at the point labeled 434 falls below the current value of the moving threshold. Accordingly, at this point the pacer/ICD (step 422 of FIG. 7) begins to accumulate the deficit 432, which increases (negatively) with each subsequent respiration cycle and soon crosses a fixed apnea/hypopnea detection threshold 436, at which point therapy is initiated. Eventually, at the point labeled 438, the amplitude of a new respiration cycle exceeds the current value of the moving threshold and so the deficit is reset (step 428 of FIG. 7). However, therapy has already been initiated.

The second graph of FIG. 10 illustrates a second set of individual amplitude values 440. The moving threshold is again shown by way of dotted line 430 and the accumulated deficit is shown by way of dashed line 432. The amplitude of the respiration cycle at point 434 again falls below the current value of the moving threshold and the pacer/ICD again begins to accumulate the deficit 432. However, in this example, the amplitude of the next respiration cycle (the point labeled 442) exceeds the current value of the moving threshold and so the accumulated deficit is immediately reset (step 428 of FIG. 7). Therefore, the accumulated deficit does not drop below the fixed detection threshold 436; apnea/hypopnea is not detected and therapy is not applied. The second graph demonstrates how the algorithm works to prevent individual low respiration amplitudes from immediately triggering therapy. By instead accumulating a deficit and comparing the accumulated deficit against a fixed threshold, false positive detections of apnea/hypopnea are substantially avoided, yet actual episodes of apnea/hypopnea are promptly detected. Separate thresholds may be used for distinguishing apnea from hypnea. In one example, a relatively high fixed threshold is employed to detect apnea whereas as relatively lower fixed threshold is used to detect hypopnea.

Thus, FIGS. 7-10 illustrate a technique wherein deficits are only accumulated so long as respiration amplitudes fall below the moving threshold. Apnea/hypopnea is detected and therapy is delivered only when the accumulated deficit crosses the fixed detection threshold. In the technique described below with reference to FIGS. 12-13, the accumulated deficit is instead accumulated at all times for comparison against dual thresholds—one for triggering therapy and one for terminating therapy. With the method of FIGS. 7-10, any of a variety of techniques may be employed for terminating the delivery of therapy after it has been initiated. For example, therapy can be terminated after some fixed period of time. Alternatively, therapy can be terminated once the amplitude of at least one individual respiration cycle exceeds a fixed episode end threshold indicating that normal respiration has resumed. As can be appreciated, a wide variety of techniques may be employed for terminating therapy.

Note that, in the foregoing, an algorithm is provided for use at step 418 of FIG. 10 to calculate the moving threshold (referred to as "thz0") based on mean and standard deviations of input values of thoracic impedance Z. The calculated value for thz0 is then used in steps 422-428 for use in determining when to initiate therapy. Alternatively, a single algorithm may be used that determines when to initiate therapy based on input values of Z as follows (i.e. this algorithm performs steps 418-428):

```
z0=0;z1=0; z2=0; % 0 is the most recent
whenever new Z detected
{
    meanz0= 0.6 *meanz1+0.4*mean(z0,z1,z2);
    e_meanz= z0-meanz0;
    if e_meanz >0,
        e_meanz =0; sum_e_meanz =0; // breath exists
    else
        e_meanz = -1 * e_meanz; // breath is below moving
threshold
        sum_e_meanz = sum_e_meanz + e_meanz
        if sum_e_meanz > preset_apnea_detection_thresh,
            INITIATE THERAPY HERE
    end;
    meanz1= meanz0;
    stdz1 = stdz0;
}
```

In this algorithm, a value for "thz0" is not explicitly calculated. Rather, meanz0 is used as the moving threshold. In general, any weighted sum based on mean and standard deviations of values of Z may potentially be employed as the moving threshold. Note also that "sum_e_meanz" represents the accumulated deficit and "preset_apnea_detection_threshold" represents the fixed detection threshold. In this case, the accumulated deficit and the fixed detection threshold are both calculated as positive values, rather than as negative values as shown FIG. 10. Accordingly, apnea/hypopnea is detected and therapy is applied if sum_e_meanz exceeds preset_apnea/hypopnea_detection_threshold.

Apnea/Hypopnea Therapy

Figure 11:
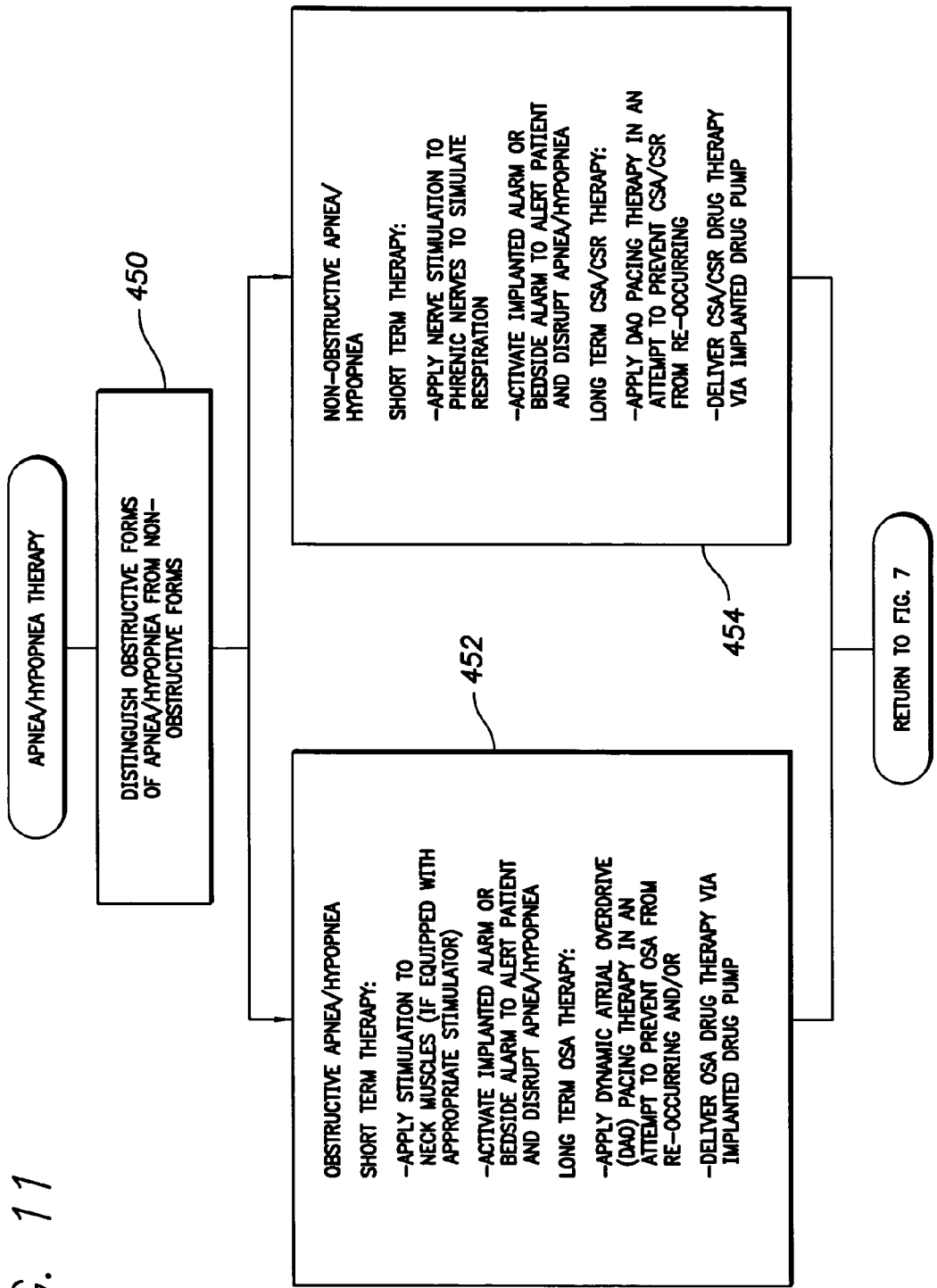
FIG. 11 is a flow diagram illustrating an exemplary method performed by the system of FIG. 7 for delivering therapy in response to the detection of apnea/hypopnea.

Exemplary therapy that may be applied once apnea/hypopnea is detected is summarized in FIG. 11. Initially, the pacer/ICD distinguishes obstructive forms of apnea/hypopnea from non-obstructive forms, at step 450. If obstructive, the therapy listed in block 452 is performed. Otherwise, the therapy listed in block 454 is performed.

Within CSA/CSR therapy block 454, two forms of apnea/hypopnea therapy are provided: long-term therapy and short-term therapy. Long-term therapy is employed at all times within patients who are subject to frequent episodes of apnea/hypopnea arising due to CSA or CSR. Short-term therapy is applied only during individual episodes of apnea/hypopnea arising due to CSA or CSR. Long-term therapy includes delivery of DAO pacing therapy in an attempt to prevent the onset of additional episodes of CSA or CSR. A particularly effective overdrive pacing technique for the atria, referred to herein as dynamic atrial overdrive (DAO) pacing, is described in U.S. Pat. No. 6,519,493, to Florio et al., entitled "Methods And Apparatus For Overdrive Pacing Heart Tissue Using An Implantable Cardiac Stimulation Device". With DAO, the overdrive pacing rate is controlled to remain generally uniform and, in the absence of a tachycardia, is adjusted upwardly or downwardly only occasionally. The aggressiveness of overdrive pacing may be modulated by adjusting the overdrive pacing rate and related control parameters. See: U.S. Patent Applications 2003/0171782 and 2003/0171781, both of Florio et al., entitled "Method And Apparatus For Using A Rest Mode Indicator To Automatically Adjust Control Parameters Of An Implantable Cardiac Stimulation Device", both published Sep. 11, 2003; U.S. Patent Application 2003/0130704, also of Florio et al., entitled "Method And Apparatus For Dynamically Adjusting A Non-Linear Overdrive Pacing Response Function", published Jan. 10, 2003; and in U.S. Patent Application 2003/0130703, also of Florio et al., entitled "Method And Apparatus For Dynamically Adjusting Overdrive Pacing Parameters", also published Jul. 10, 2003. These DAO applications are incorporated by reference herein. Preferably, parameters for controlling DAO therapy are set to values appropriate for reducing the likelihood of additional episodes of apnea/hypopnea. Routine experimentation and may be performed to identify optimal DAO pacing parameters for use with patients with CSA or CSR. The aggressiveness of DAO therapy may be adjusted based upon the frequency or duration of episodes of CSA or CSR.

Long-term therapy for apnea/hypopnea arising due to CSA or CSR also includes the delivery of appropriate medications via an implantable drug pump, if so equipped. Examples of medications that may be helpful in patients with apnea/hypopnea are set forth the following patents: U.S. Pat. No. 6,331,536 to Radulovacki, et al., entitled "Pharmacological Treatment for Sleep Apnea"; U.S. Pat. No. 6,432,956 to Dement, et al., entitled "Method for Treatment of Sleep Apneas"; U.S. Pat. No. 6,586,478 to Ackman, et al., entitled "Methods and Compositions for Improving Sleep"; and U.S. Pat. No. 6,525,073 to Mendel, et al., entitled "Prevention or Treatment of Insomnia with a Neurokinin-1 Receptor Antagonist". Depending upon the particular medication, alternative compounds may be required for use in connection with an implantable drug pump. Routine experimentation may be employed to identify medications for treatment of apnea/hypopnea that are safe and effective for use in connection with an implantable drug pump. Dosages may be titrated based upon the frequency or duration of episodes of CSA or CSR.

Short-term therapy for individual episodes of apnea/hypopnea arising due to CSA or CSR includes delivery of PNS to the phrenic nerves (via stimulators 12 of FIG. 1) to simulate breathing. Examples of phrenic nerve stimulators are set forth in the aforementioned patents to Vince and Scheiner, et al. Other respiratory nerves may be stimulated as well. U.S. Pat. No. 5,911,218 to DiMarco, entitled "Method and Apparatus for Electrical Stimulation of the Respiratory Muscles to Achieve Artificial Ventilation in a Patient" describes stimulation of nerves leading to intercostal muscles. These patents are incorporated by reference herein. If phrenic nerve stimulators are not implanted or are otherwise ineffective in simulating breathing during an episode of apnea/hypopnea, then an implantable apnea/hypopnea alarm (such as alarm 18 of FIG. 1) is preferably activated to alert and, if sleeping, awaken the patient to terminate the episode of apnea/hypopnea. Alternatively, a bedside alarm may be activated by transmission of appropriate wireless control signals. Activation of an alarm to alert the patient while asleep is preferably employed only if other forms of long-term or short-term therapy are found to be ineffective, since awakening the patient interrupts with the patient's natural sleeping patterns. In any case, whenever some form of apnea/hypopnea therapy is delivered, appropriate diagnostic information is stored so that a medical professional can subsequently review the therapy and evaluate its effectiveness.

Therapy for obstructive forms of apnea/hypopnea is summarized in block 452. Again, two forms of therapy are provided: long-term therapy and short-term therapy. Long-term therapy is employed at all times within patients subject to frequent periods of obstructive apnea/hypopnea whereas short-term therapy is applied only during individual episodes of obstructive apnea/hypopnea. Long-term therapy includes delivery of DAO pacing therapy in an attempt to prevent the onset of additional episodes of apnea/hypopnea. Again, preferably, the parameters for controlling DAO therapy are set to values appropriate for reducing the likelihood of additional episodes of apnea/hypopnea and routine experimentation may be performed to identify such optimal parameters. Note that the specific parameters for controlling DAO therapy to prevent the onset of obstructive forms of apnea/hypopnea may differ from the parameters for controlling DAO to prevent the onset of CSA. Hence, if a particular patient is only subject to OSA, but not CSA, a different set of control parameters may be employed than if the patient is subject to both. Long-term therapy also includes delivery of appropriate medications via an implantable drug pump, if so equipped, such as the medications described in the patents listed above. In many cases, no distinction is made between CSA and OSA with respect to medications. In circumstances where a medication may be safe and effective only for use with OSA but not CSA, the drug pump is controlled to deliver only the appropriate medication. Again, dosages may be titrated based upon the frequency or duration of episodes of obstructive forms of apnea/hypopnea.

Short-term therapy includes delivery of stimulation to the muscles near the soft palate (via stimulators 16 of FIG. 1) in an attempt to improve muscle tone to open the blocked airway. Muscle stimulators for delivering therapy in response to OSA are set forth in: U.S. Pat. No. 6,345,202 to Richmond, et al., entitled "Method Of Treating Obstructive Sleep Apnea Using Implantable Electrodes"; U.S. Pat. No. 6,240,316 also to Richmond, et al., entitled "Implantable Microstimulation System For Treatment Of Sleep Apnea"; and U.S. Pat. No. 6,587,725 to Durand, et al., entitled "Method And Apparatus For Closed-Loop Stimulation Of The Hypoglossal Nerve In Human Patients To Treat Obstructive Sleep Apnea". These patents are also incorporated by reference herein. If such stimulators are not implanted or are otherwise ineffective during an episode of OSA, then the implantable apnea/hypopnea alarm or external bedside alarm is preferably activated to alert or awaken the patient. Again, activation of an alarm to awaken the patient is preferably employed only if other forms of long-term or short-term therapy are found to be ineffective. In any case, whenever some form of OSA therapy is delivered, appropriate diagnostic information is stored.

If the pacer/ICD is not equipped to distinguish among the different forms of apnea/hypopnea, general therapy is provided instead. For example, DAO therapy or drug therapy is delivered and/or alarm signals are generated. In this case, stimulation signals are preferably not applied to the phrenic nerves or to neck muscles since it is not known whether such stimulation would be applicable to the current episode of apnea/hypopnea.

Exemplary Detection and Response Technique with Dual Thresholds

Figure 12:
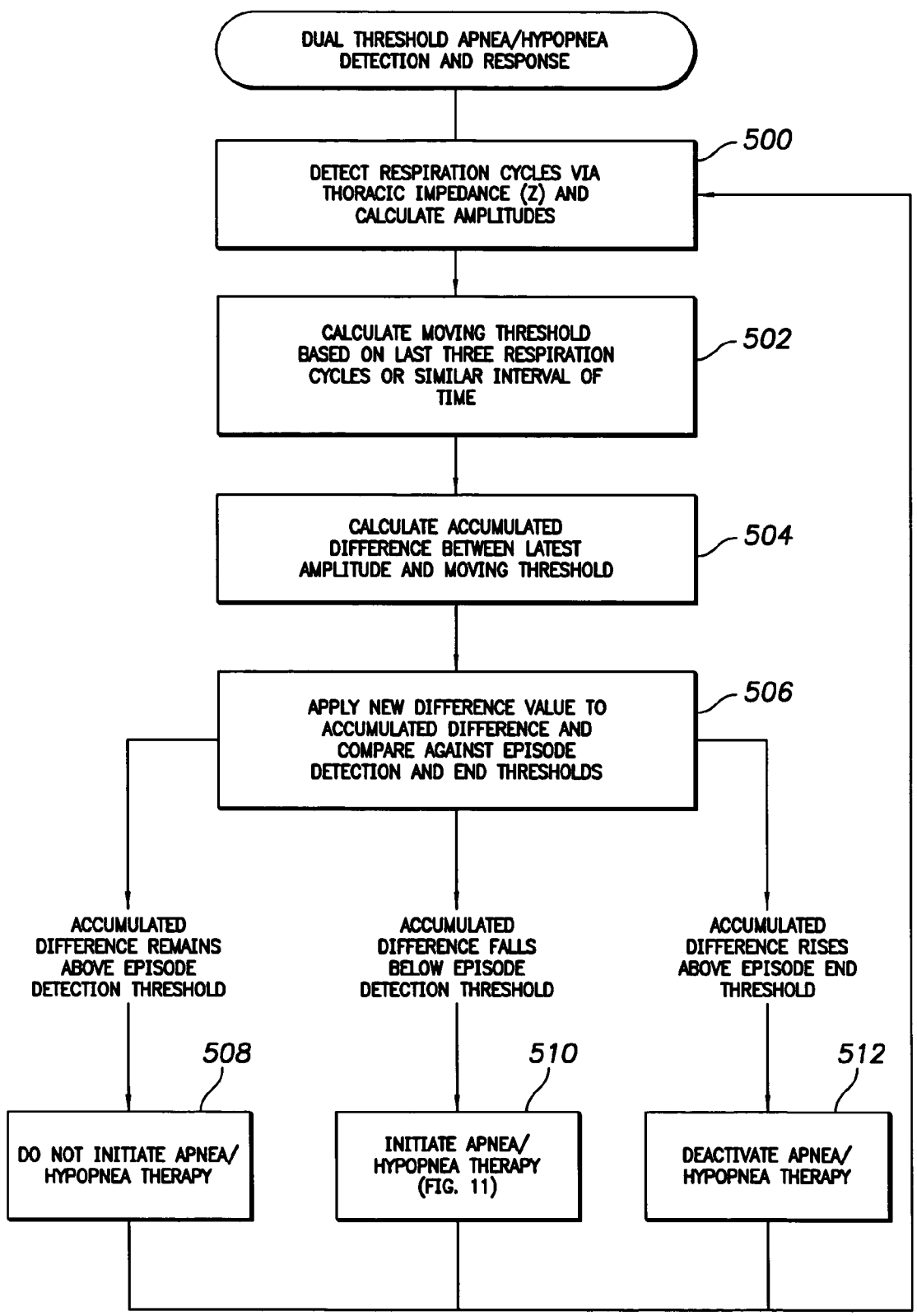
FIG. 12 is a flow diagram illustrating an alternative method performed by the system of FIGS. 4-6 for detecting apnea/hypopnea, which employs dual thresholds.

With respect to the remaining figures, an alternative technique for detecting apnea/hypopnea is set forth. In the alternative technique, the accumulated deficit is calculated at all times (rather than only while respiration amplitudes fall below the moving threshold). The accumulated deficit is compared against dual thresholds—one for triggering therapy and one for terminating therapy. The technique is primarily illustrated in the flowchart of FIG. 12. Several of the steps of FIG. 12 are similar to those of technique of FIG. 7 and only pertinent differences will be described in detail. At step 500, the pacer/ICD detects respiration cycles using thoracic impedance and calculates the amplitudes of the respiration cycles. Amplitudes are calculated using the same technique as described above wherein the derivative of the impedance signal is calculated and areas under the derivative signal between consecutive zero crossing points corresponding to transitions from valleys to peaks are summed. The pacer/ICD, at step 502, then calculates the moving threshold based upon the most recent respiration cycles using techniques described above. At step 504, a difference between the amplitude of the most recent respiration cycle and the moving threshold is calculated. If the amplitude exceeds the moving threshold, the difference is thereby a positive number. If the amplitude is below the moving threshold, the difference is a negative number.

At step 506, the latest difference value is applied to previously accumulated difference values and then compared against a fixed episode detection threshold and a fixed episode end threshold. Depending upon the circumstances, the accumulated difference may be a positive or a negative number. For example, if respiration amplitudes have remained above the moving threshold for some time, then the accumulated difference will be a positive number. However, if respiration amplitudes have remained below the moving threshold for some time, then the accumulated difference will be a negative number. The episode detection threshold is a fixed negative number. The episode end threshold is a fixed positive number. So long as the accumulated difference remains above the negative episode detection threshold, no therapy is applied (step 508). If the accumulated difference crosses from above the episode detection threshold to below the episode end threshold, apnea/hypopnea is thereby detected and therapy is activated (step 510). Therapy may be applied in accordance with the general techniques described above with reference to FIG. 11. Thereafter, if the accumulated difference crosses from below the episode detection threshold to above the episode end threshold, the end of the episode of apnea/hypopnea is thereby detected and therapy is deactivated (step 512). As with the techniques provided above, separate fixed thresholds may be provided for separately detecting hypopnea and apnea. In one example, separate episode detection and end thresholds are provide for both hypopnea and apnea. In other words, at least four fixed threshold are employed.

Figure 13:
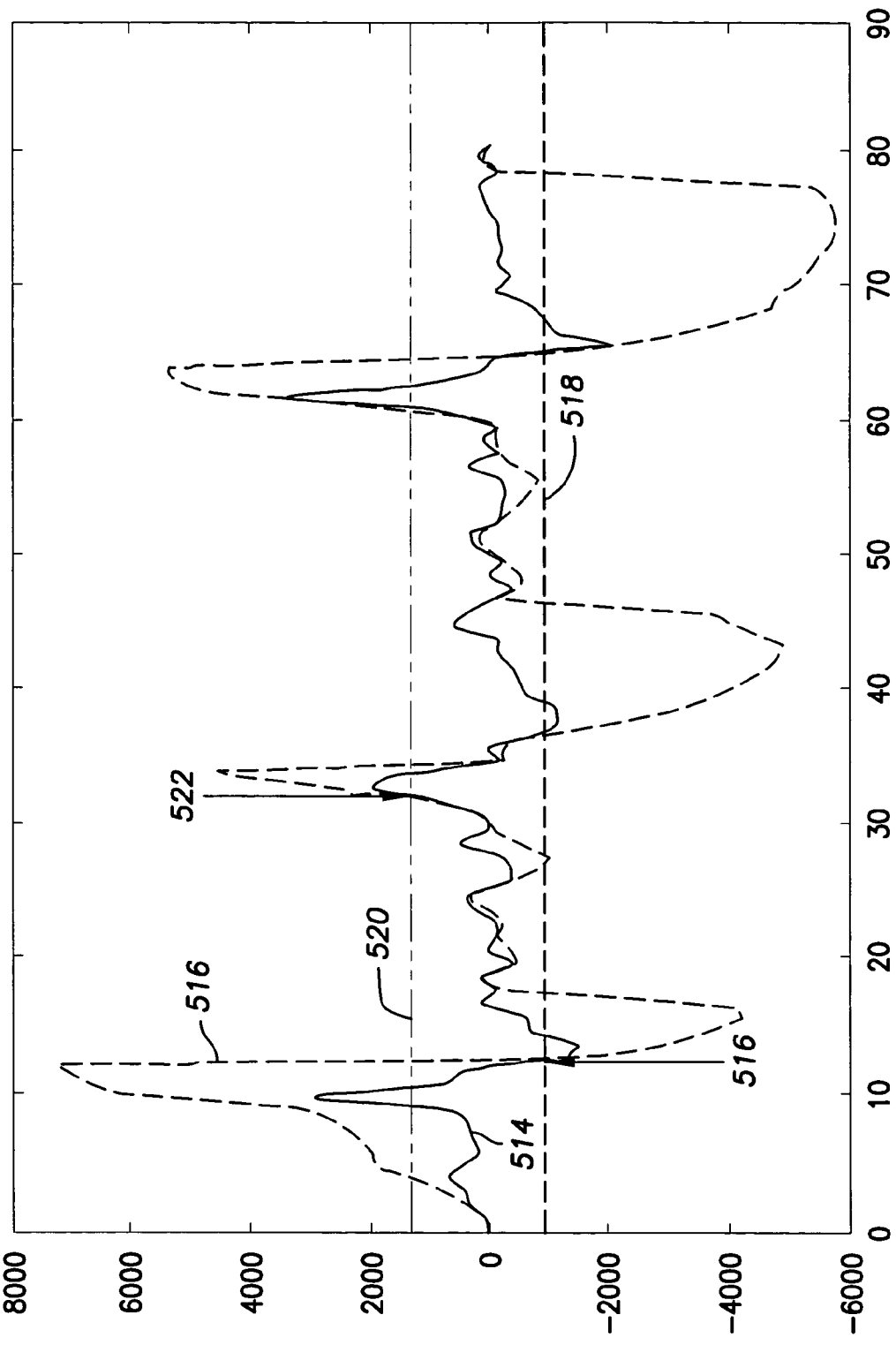
FIG. 13 is a graph illustrating exemplary respiration amplitude values, accumulated deficit values, and dual thresholds used in the method of FIG. 12.

The procedure of FIG. 12 is illustrated by way of the example of FIG. 13. In the example of FIG. 13, the amplitude of individual respiration cycles are not shown, nor is the moving threshold explicitly shown. Rather, FIG. 13 illustrates the current difference between respiration amplitudes and the moving threshold by way of solid line 514 and represents the accumulation of those differences by way of dotted line 516. As can be seen, the current difference varies from positive values to negative values. While positive, individual respiration amplitudes are above the current value of the moving threshold. While negative, individual respiration amplitudes are below the current value of the moving threshold. It is during periods when the difference is negative that apnea/hypopnea may be present. While the difference is positive (time 0 to time 10), the accumulated differences (curve 516) increase to large positive numbers. However, once the current difference becomes negative (after time 10), the accumulated difference quickly shifts to negative numbers. At point 516, the accumulated difference falls below a negative fixed apnea/hypopnea therapy initiation threshold 518. At that point, apnea/hypopnea is detected and therapy is applied. Eventually, the numerical value of the accumulated difference increases from negative values to positive values until it exceeds a positive fixed episode end threshold 520 at point 522, at which time therapy is terminated. In the specific example of FIG. 13, the patient is suffering from CSR, hence the accumulated difference curve cycles from a large positive numbers during the hyperpnea phase of CSR to large negative numbers during the hypopniec/apneic phase of CSR, thus repeatedly and cyclically triggering therapy.

The techniques of FIGS. 12-13 may be used in systems employing PNS therapy. Note, however, that the immediate increase in respiration amplitudes caused by PNS may affect use of the apnea/hypopnea episode end threshold. Nevertheless, the technique is still beneficial in determining when to activate PNS.

What have been described are various systems and methods for detecting apnea/hypopnea and delivering therapy in response thereto using an implantable system controlled by a pacer or ICD. However, principles of the invention may be exploiting using other implantable systems or in accordance with other techniques. Thus, while the invention has been described with reference to particular exemplary embodiments, modifications can be made thereto without departing from the spirit and scope of the invention.

What is claimed is:

1. A method for detecting the onset of an episode of reduced respiration within a patient using an implantable medical device, the method comprising:

generating a moving threshold based on recent respiration cycles;

accumulating a sum of the differences between amplitudes of new respiration cycles and the moving threshold; and detecting the onset of an episode of reduced breathing based upon the accumulated differences.

2. The method of claim 1 wherein detecting the onset of an episode of reduced breathing is performed to detect one or more of apnea and hypopnea.

3. The method of claim 1 wherein generating a moving threshold is performed based on a predetermined number of respiration cycles.

4. The method of claim 3 wherein the predetermined number of respiration cycles is three.

5. The method of claim 1 wherein generating a moving threshold is performed based on respiration cycles detected within a predetermined fixed interval of time.

6. The method of claim 1 wherein generating a moving threshold based on recent respiration cycles is performed using thoracic impedance values and wherein the method further comprises:

activating a timer after detection of each new respiration cycle; and if the timer expires before a next respiration cycle is detected, updating the moving threshold based on recent thoracic impedance values regardless of whether the thoracic impedance values conform to an identifiable respiration cycle.

7. The method of claim 1 wherein the moving threshold is based on weighted combinations of mean and standard deviations in amplitudes of the recent respiration cycles.

8. The method of claim 1 wherein generating the moving threshold comprises:

calculating amplitude values associated with each of the recent respiration cycles;

calculating mean values associated with each of the recent respiration cycles;

calculating standard deviation values associated with each of the recent respiration cycles; and calculating the moving threshold based on weighted sums of the mean values and the standard deviation values.

9. The method of claim 8 wherein calculating amplitude values comprises:

tracking thoracic impedance Z(t) using leads implanted within the chest;

calculating the derivative (dZ/dt) of thoracic impedance;

identifying respiration cycles by identifying consecutive zero crossing points in the derivative of thoracic impedance that are associated with inspiration; and calculating the amplitude of a respiratory cycle by integrating the derivative of the thoracic impedance between consecutive zero crossing points associated with inspiration.

10. The method of claim 1 wherein accumulating differences between amplitudes of new respiration cycles and the moving threshold is performed only while the amplitudes of the new respiration cycles fall below the moving detection threshold.

11. The method of claim 1 wherein detecting the onset of an episode of reduced respiration based upon the accumulated differences is performed by comparing the accumulated differences against a fixed detection threshold.

12. The method of claim 1 wherein accumulating differences between amplitudes of respiration cycles and the moving threshold is performed substantially continuously.

13. The method of claim 1 wherein detecting the onset of an episode of reduced respiration based upon the accumulated differences is performed by comparing the accumulated differences against a fixed episode detection threshold.

14. The method of claim 13 further comprising detecting the end of an episode of reduced respiration based upon the accumulated differences by comparing the accumulated differences against a fixed episode end threshold.

15. The method of claim 1 further comprising delivering therapy upon detection of an episode of reduced respiration.

16. The method of claim 15 wherein the implantable device is equipped to deliver overdrive pacing therapy to the heart of the patient and wherein delivering therapy comprises delivering overdrive pacing therapy to the heart of the patient.

17. The method of claim 16 wherein the overdrive pacing therapy is dynamic atrial overdrive (DAO) pacing therapy.

18. The method of claim 15 wherein an implantable drug pump is provided and wherein delivering therapy comprises selectively delivering drug therapy to the patient using the drug pump.

19. The method of claim 15 further comprising determining whether a current episode of reduced respiration is associated with central sleep apnea (CSA).

20. The method of claim 19 for use with a system having an implantable phrenic nerve sensor and wherein determining whether the current episode of reduced respiration is associated with CSA is performed based on the signals received from the phrenic nerve sensor.

21. The method of claim 19 for use with a system having an implantable phrenic nerve stimulator and wherein, if the episode of reduced respiration is associated with CSA, therapy includes application of stimulation to the phrenic nerves using the phrenic nerve stimulator.

22. The method of claim 15 further comprising determining whether a current episode of reduced respiration is associated with obstructive sleep apnea (OSA).

23. The method of claim 22 for use with a system having an implantable phrenic nerve sensor and wherein determining whether the current episode of reduced respiration is due to OSA is performed based on the signals received from the phrenic nerve sensor.

24. The method of claim 22 for use with a system having an implantable upper airway sensor and wherein determining whether the current episode of reduced respiration is associated with OSA is performed based on signals received from the upper airway sensor.

25. The method of claim 22 for use with a system having an implantable upper airway stimulator mounted near the soft palate of the patient and wherein, if the episode of reduced respiration is associated with OSA, therapy includes application of stimulation to the muscles near the soft palate using the upper airway stimulator.

26. The method of claim 15 further comprising determining whether a current episode of reduced respiration is associated with Cheyne-Stokes Respiration (CSR).

27. The method of claim 26 wherein determining whether the current episode of reduced respiration is associated CSR is performed based on detection of alternating cycles of relatively reduced and increased breathing.

28. The method of claim 26 for use with a system having an implantable phrenic nerve stimulator and wherein, if the episode of reduced respiration is associated with CSR, therapy includes application of stimulation to the phrenic nerves using the phrenic nerve stimulator.

29. The method of claim 1 further comprising generating a warning signal in response to an episode of reduced respiration sufficient to alert the patient.

30. The method of claim 29 wherein generating a warning signal comprises one or more of: transmitting a signal to an external alarm device; electrically stimulating selected muscles of the patient to cause the muscles to twitch using an implantable electrical stimulator; and controlling an implantable device to vibrate.

31. The method of claim 1 for use with a system having an implantable blood oxygen sensor and further comprising confirming detection of the episode of reduced respiration based on signals received from the blood oxygen sensor.

32. The method of claim 1 further comprising recording diagnostic information representative of episodes of reduced respiration.

33. A system for detecting an episode of substantially reduced respiration within a patient using an implantable medical device, the system comprising:

circuitry operative to receive signals representative of amplitudes of respiration cycles; and a detection unit operative to detect an episode of reduced respiration based upon an accumulating a sum of the differences between amplitudes of new respiration cycles and a moving threshold generated based on the amplitudes of previous respiration cycles.

34. A system for detecting an episode of substantially reduced respiration within a patient using an implantable medical device, the system comprising:

means for detecting amplitudes of respiration cycles;

means for generating a moving threshold based on amplitudes of recent respiration cycles;

means for accumulating a sum of the differences between amplitudes of new respiration cycles and the moving threshold; and means for detecting the onset of an episode of substantially reduced breathing based upon the accumulated differences.

* * * * *